(12) United States Patent
Revie et al.

(10) Patent No.: US 7,814,916 B2
(45) Date of Patent: Oct. 19, 2010

(54) IMPLANTABLE MARKER, INSTRUMENTS AND METHODS

(76) Inventors: Ian Revie, Tutt House, New Row, Boroughbridge, N. Yorkshire (GB) Y051 9AX; Alan Ashby, 19 Clifton Green, York (GB) YO30 6LN; Yaacov Nitzan, 42/1 Hauliya Rd, Hertzeliya, YN (IL); Paul Gibbons, 29 Main Street, Addingham, Ilkley (GB) LS29 OPD; Ben Stungo, 28 St Marks Avenue, Harrogate (GB) HG2 8AE; Robert Butcher, 1 Plantation Avenue, Leeds, Alwoodley (GB) LS17 8TB; Tom Patterson, 55 Rosebury Drive, Longbenton, Newcastle-Upon-Tyne (GB) NE12 8RG; Jury Baldewein, c/o DePuy 1-Orthopaedics, Ammerthalstr. 3, 85551, Helmstetten (DE); James Brooks, c/o DePuy International Ltd., Number One, White Rose Office Park, Millshaw Park Lane, Leeds (GB) LS11 0EA ( * ) Notice: Subject to any disclaimer, the term of this patent is extended or adjusted under 35 U.S.C. 154(b) by 520 days.

(21) Appl. No.: 10/598,593

(22) PCT Filed: Mar. 7, 2005

(86) PCT No.: PCT/GB2005/000855
§ 371 (c)(1),
(2), (4) Date: Nov. 15, 2007

(87) PCT Pub. No.: WO2005/084572
PCT Pub. Date: Sep. 15, 2005

(65) Prior Publication Data
US 2008/0121242 A1 May 29, 2008

(30) Foreign Application Priority Data
Mar. 5, 2004 (GB) ................. 0405013.4

(51) Int. Cl.
A61B 19/00 (2006.01)
(52) U.S. Cl. ........................................ 128/899
(58) Field of Classification Search ........... 128/899; 600/300, 414, 423, 426
See application file for complete search history.

(56) References Cited

U.S. PATENT DOCUMENTS 4,878,915 A 11/1989 Brantigan et al.

(Continued)

FOREIGN PATENT DOCUMENTS

EP 146699 A1 7/1985

*Primary Examiner*—Charles A Marmor, II
*Assistant Examiner*—Christine D Hopkins

(57) ABSTRACT

An implantable marker, instruments for implanting the marker and method for implanting the marker are described. The implantable marker comprises a housing with an outer surface providing a bone anchor and having a cavity within which a marker detectable by a tracking system is secured. The kit includes a guide instrument having a guide channel for receiving an implantable marker, an insertion tool receivable within the channel and having a distal end for releasably engaging an implantable marker, and an implantable marker receivable within the channel. The insertion tool is operable to drive the implantable marker into the bone. The method includes puncturing the skin with an instrument, driving the implantable marker into the bone and withdrawing the instrument, leaving the marker implanted within the bone.

35 Claims, 15 Drawing Sheets

U.S. PATENT DOCUMENTS

| | | |
|---|---|---|
| 5,807,252 A | 9/1998 | Hassfeld et al. |
| 6,499,488 B1 | 12/2002 | Hunter et al. |
| 7,416,533 B2 * | 8/2008 | Gellman et al. ............ 600/562 |
| 2003/0023161 A1 | 1/2003 | Govari et al. |
| 2003/0120150 A1 | 6/2003 | Govari |
| 2004/0030236 A1 | 2/2004 | Mazzocchi et al. |

* cited by examiner

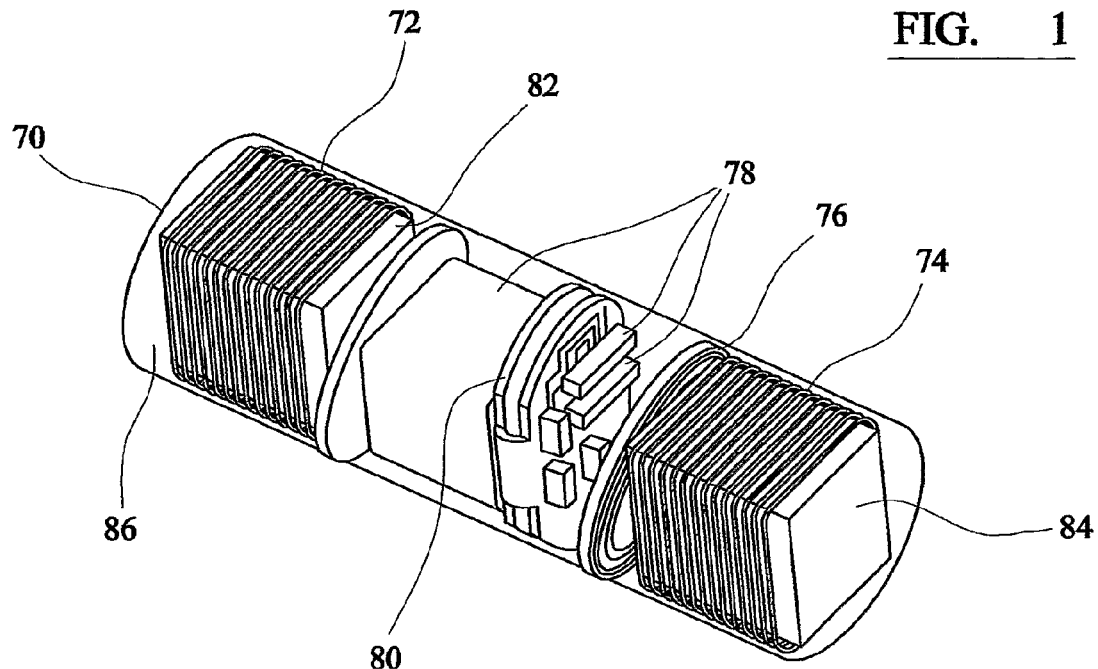
FIG. 1
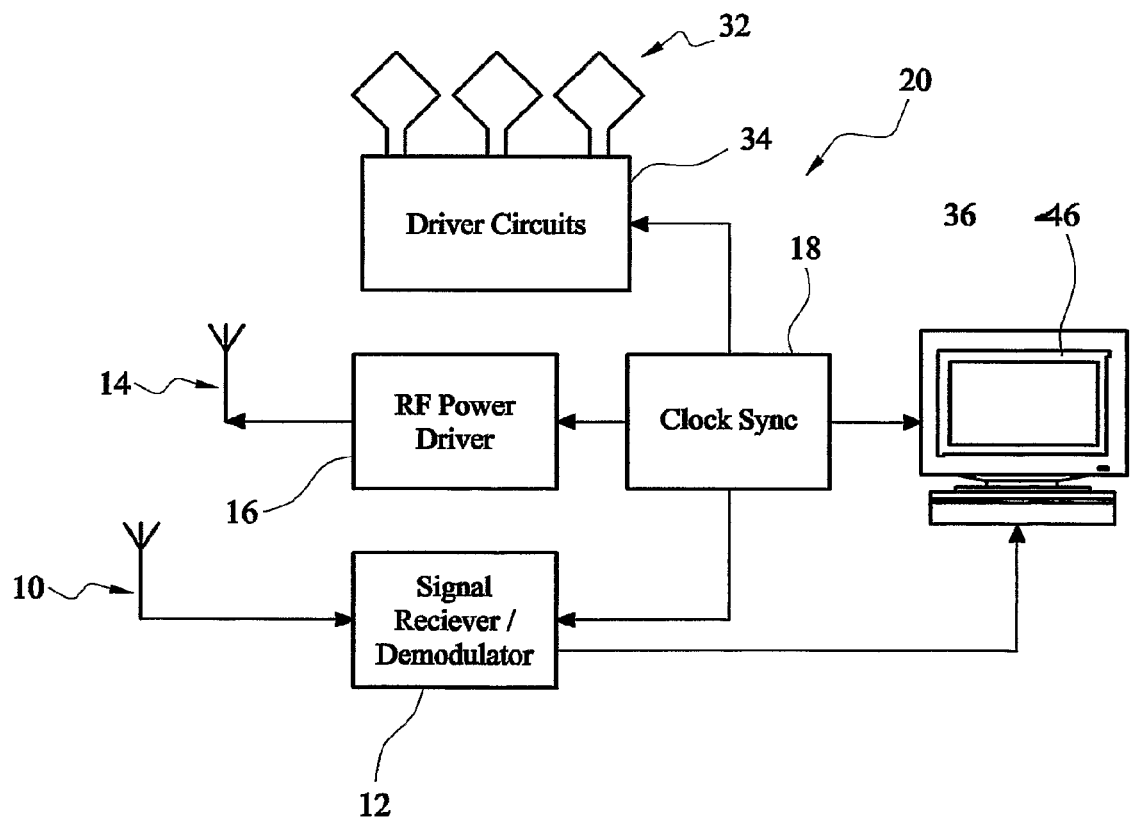

FIG. 3A
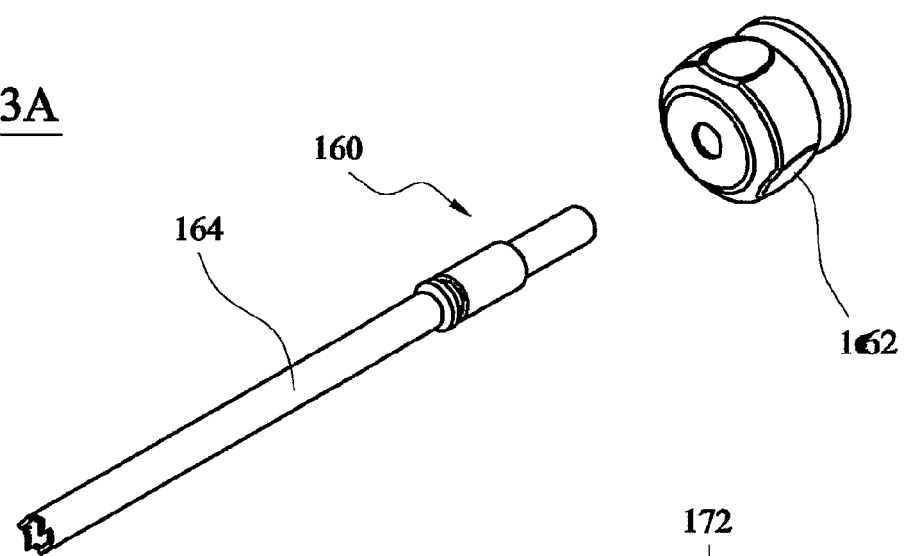
FIG. 3B
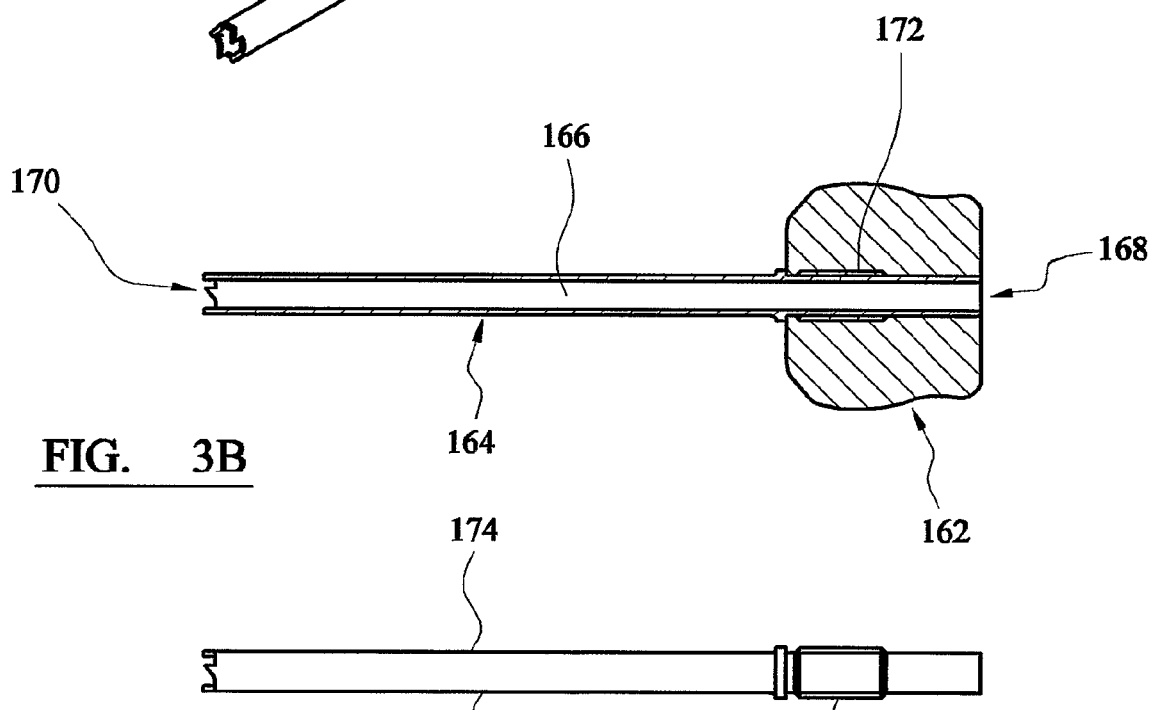
FIG. 3C
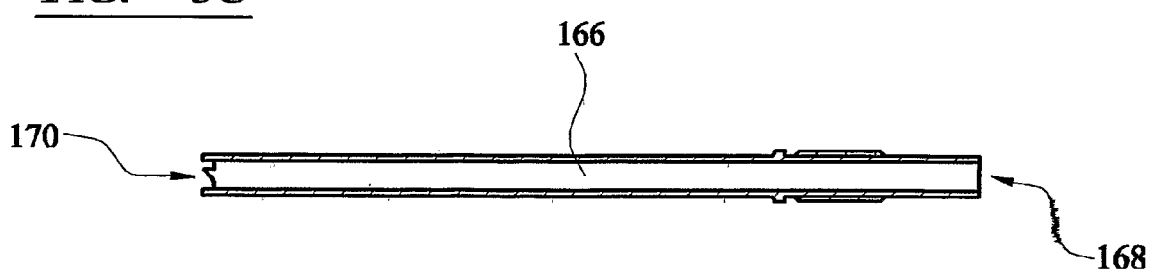
FIG. 3D

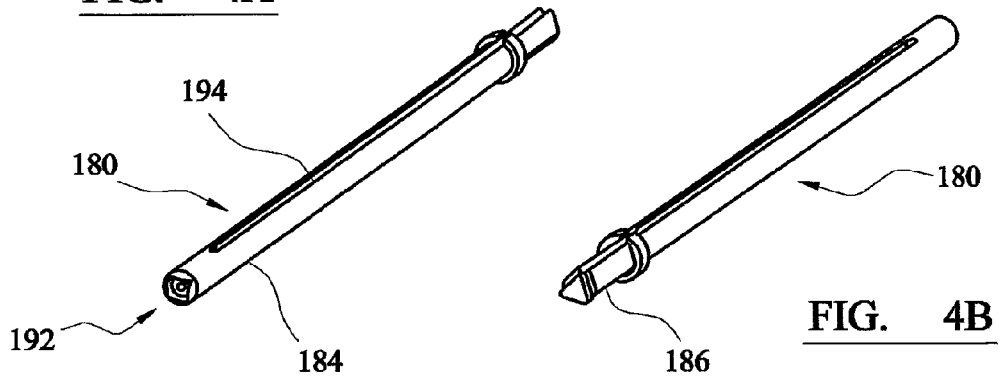
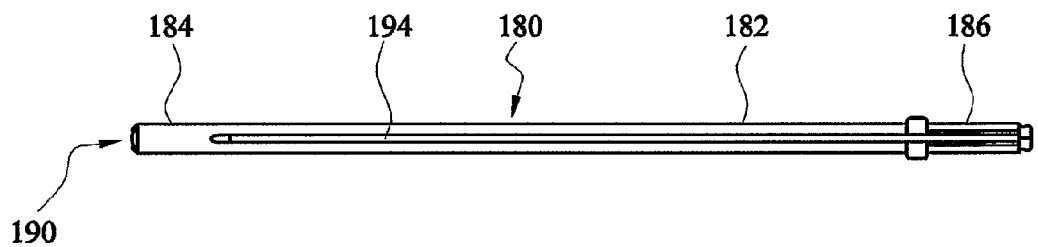
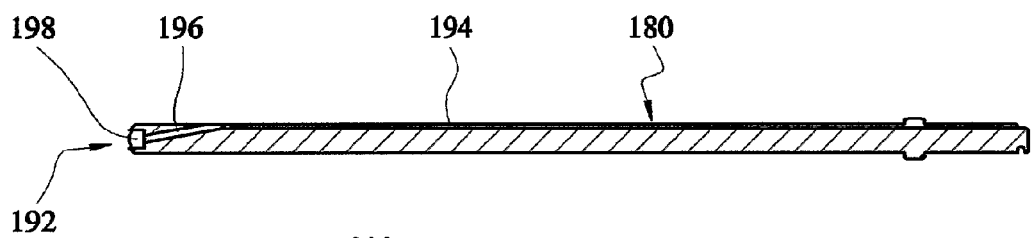
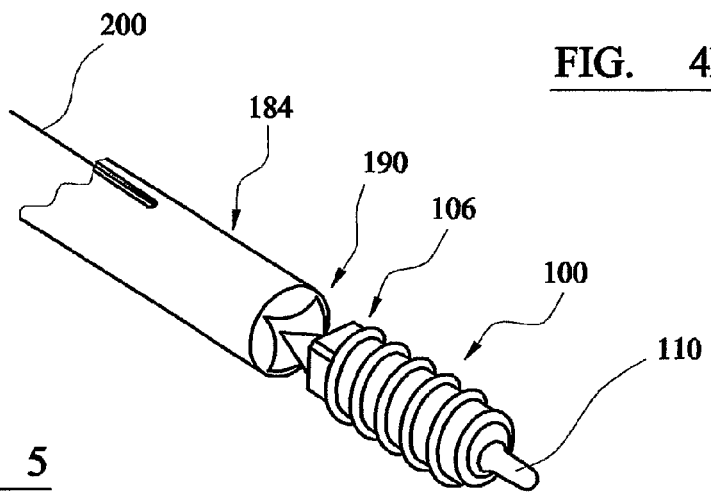

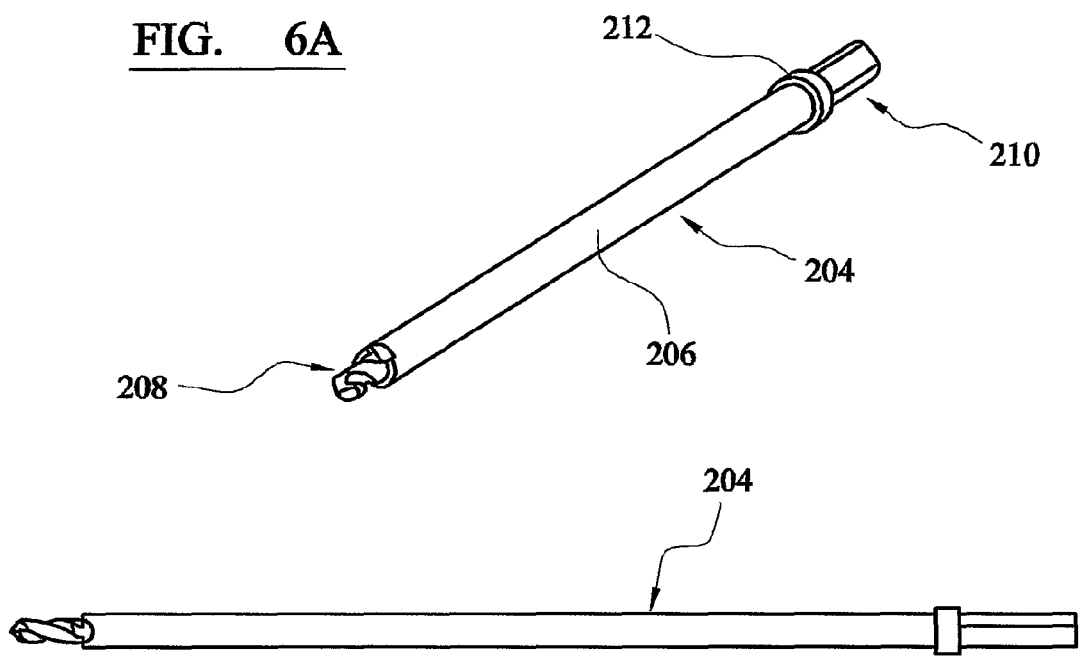
FIG. 6A
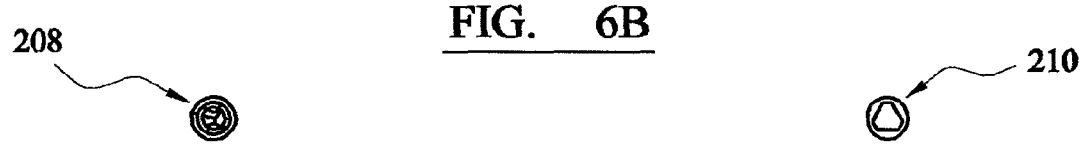
FIG. 6B
FIG. 6C
FIG. 6D
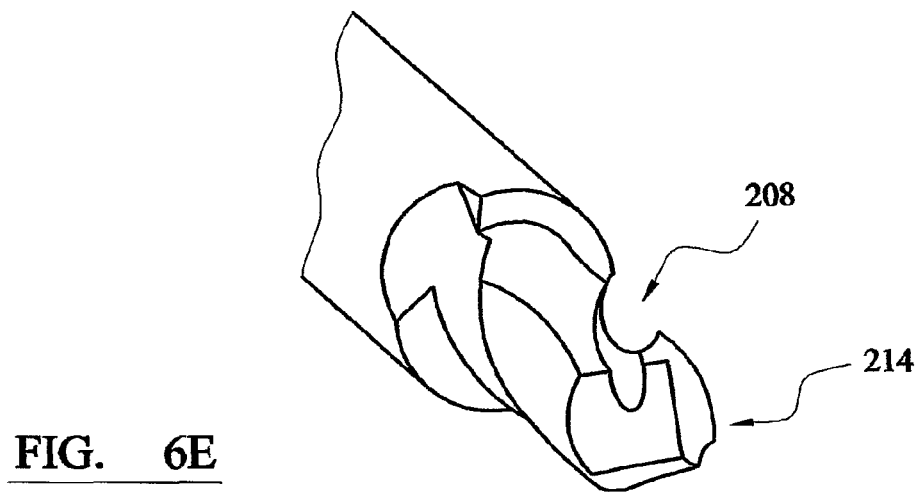
FIG. 6E

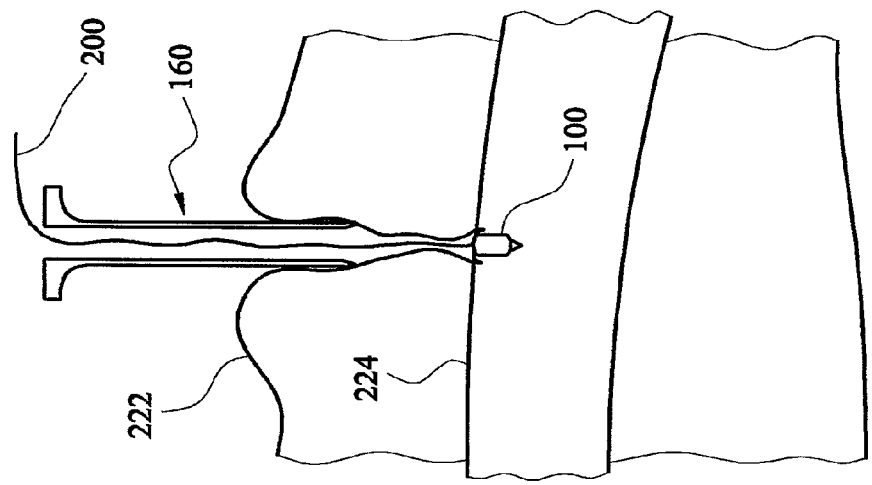
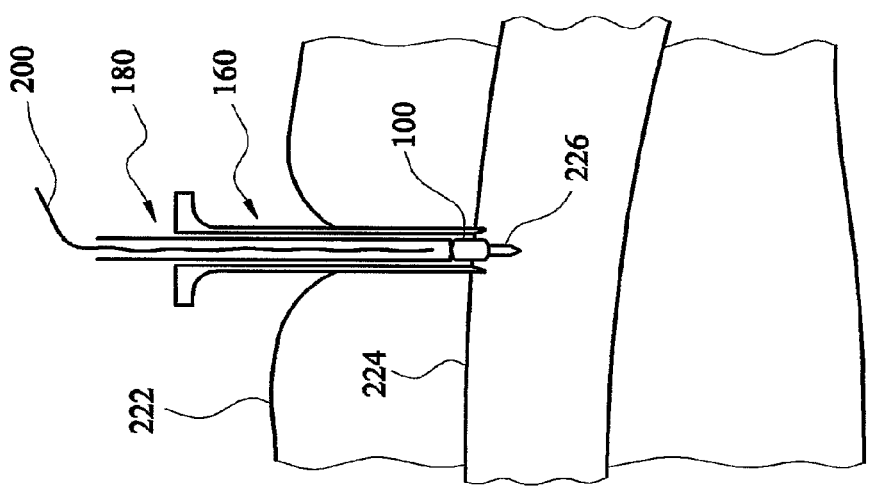
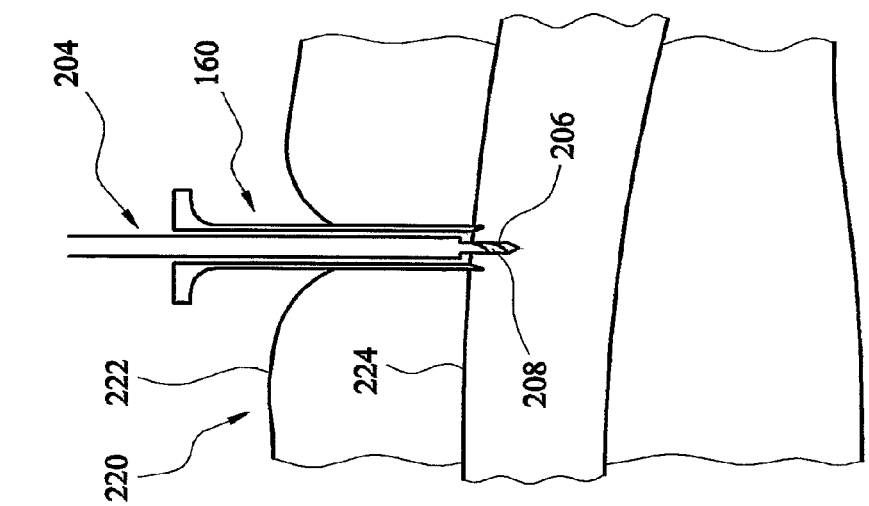
FIG. 7C
FIG. 7B
FIG. 7A

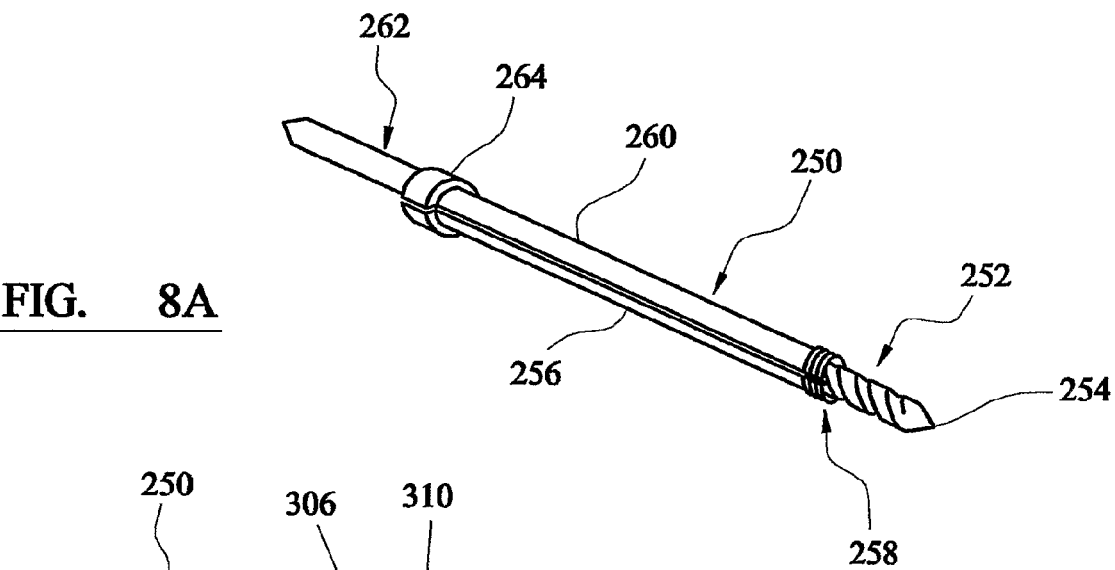
FIG. 8A
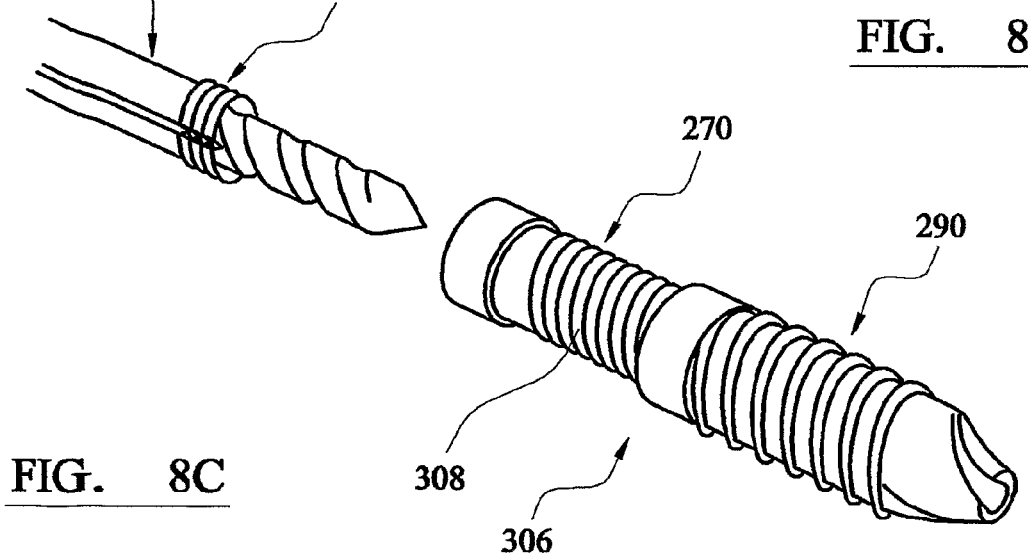
FIG. 8B
FIG. 8C

FIG. 8D
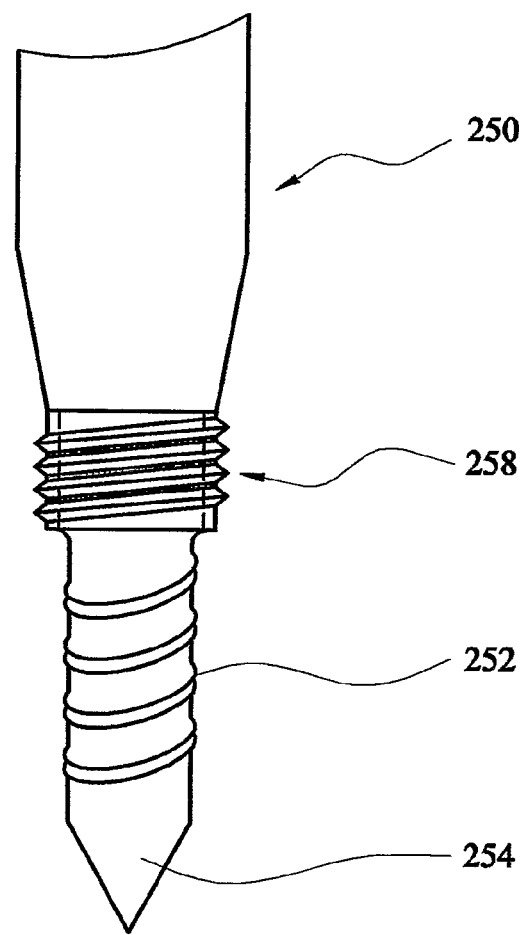
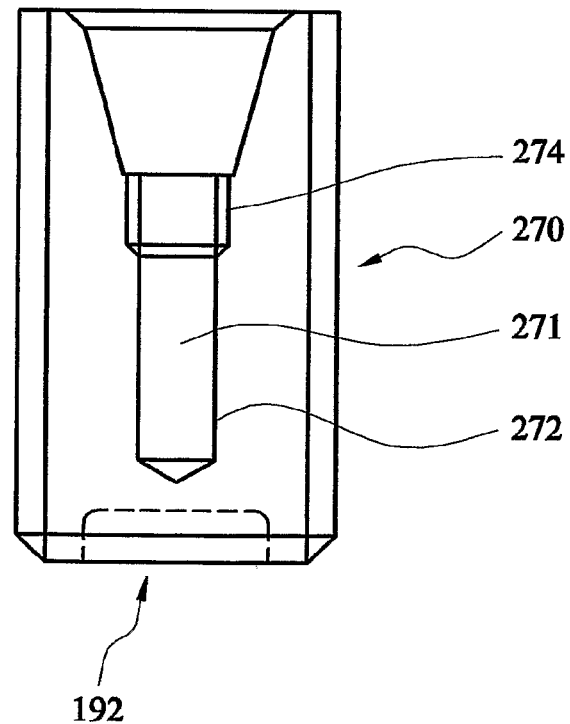

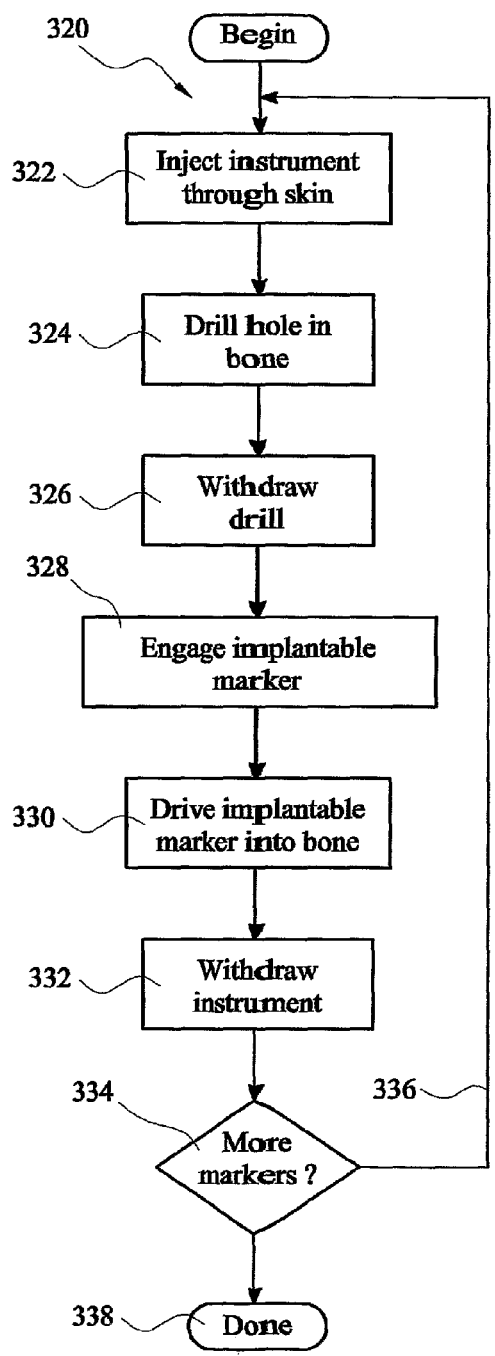
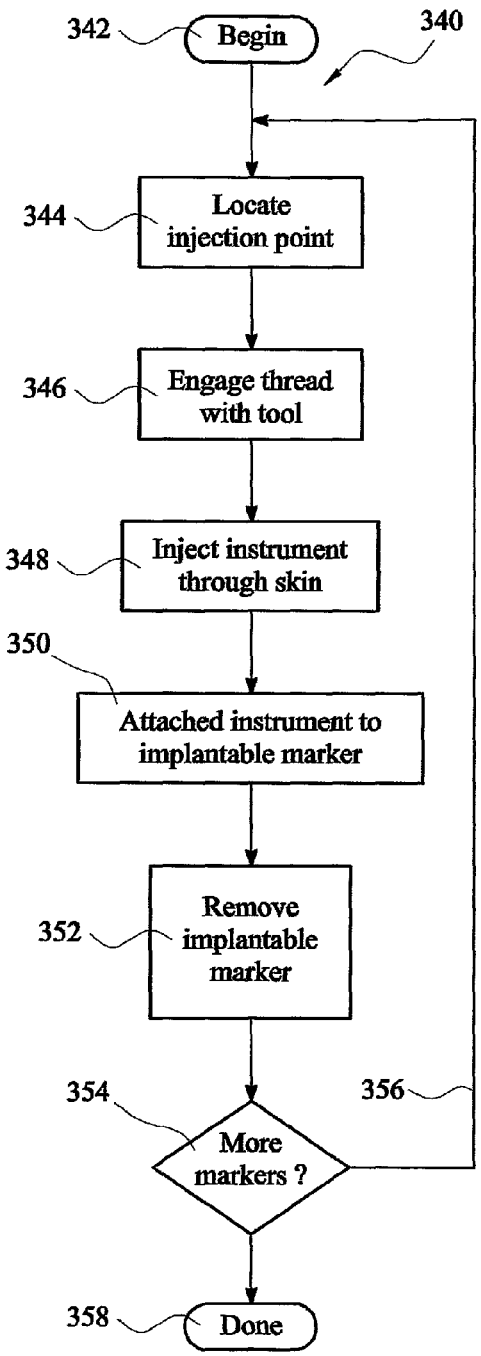
FIG. 11
FIG. 13

IMPLANTABLE MARKER, INSTRUMENTS AND METHODS

The present invention relates to markers, instruments and related methods, and in particular to a marker implantable in bone, instruments for implanting the marker, methods of implanting a marker in bone and methods using an implanted marker.

Markers detectable by a tracking system can be attached to a body part so that the position of the body part can be tracked, e.g., during a surgical procedure. Such markers are sometime referred to as fiducial markers. A variety of marker types can be used depending on the nature of the tracking system and how signals are generated by the marker and communicated to the tracking system. However, markers are typically provided on some kind of support structure by which the marker is mounted on the body part, such as on the skin, or anchored to bone or another subcutaneous body part or anatomical structure.

However, there can be problems associated with mounting a marker on the body using a support structure. There can be a greater chance for discrepancy between the detected position of the marker and the position of the body part that the marker is associated with and the position of which is derived from the detected marker position. Further, when mounting a marker on bone, an incision is made so as to gain access to the bone for attaching the marker support and so there is an increase in trauma suffered by the patient. Furthermore, the attachment of markers complicates and lengthens the surgical procedure as the attachment of markers is typically carried out as a separate procedure preceding the actual surgical procedure for which the markers are required.

An example surgical sensor is described in U.S. Pat. No. 6,499,488 (Hunter et al.) in which a sensor, which sends signals to a surgical guidance system, is provided in a housing mounted on a surgical screw, or in a hollow part of the screw in lieu of the housing. The surgical screw can be screwed into a bony anatomical structure. Hence, the sensor is attached to a bony anatomical structure by the screw. However, the sensor is still supported by the screw and the sensor is not itself located in the bony structure. Further, an incision is still required in order to attach the sensor to the body part.

The present invention therefore addresses various deficiencies in markers.

According to a first aspect of the present invention, there is provided an implantable marker for percutaneously implanting within a bone. The implantable marker comprises a housing having an inner cavity and a marker secured within the cavity. The housing can have an outer surface providing a bone anchor. The bone anchor can engage at least partially with surrounding bone when implanted to retain the implantable marker in the bone. The marker can be detectable by a tracking system.

As the implantable marker can be implanted in bone through the skin of the patient, without requiring a preliminary incision, i.e. the implantable marker is percutaneously implantable, the surgical trauma experienced by a patient is reduced.

The patient can be mammalian, and can be an animal or a human.

The marker and cavity can be configured such that at least a part of the marker is positioned within the bone in use. Preferably a position detecting part of the marker is located within the bone of the patient.

The whole of the implantable marker can be implanted within the bone. That is, no part of the implantable marker can be proud of the outer surface of the bone when the implantable marker has been implanted.

The marker can be hermetically sealed. The housing can be hermetically sealed. Both the housing and the marker can be hermetically sealed. This helps to increase the time during which the implanted marker can be left in a patient.

The bone anchor can be in the form of a retaining formation. The retaining formation can be a single structure or a plurality of structures. The retaining formation can be in the form of ribs, teeth, prongs, barbs, troughs, lips or any other formation which can engage with surrounding bone material to help retain the implantable marker in a bone in use.

The bone anchor can be provided by a surface adapted to encourage, enhance. promote or otherwise facilitate bone ongrowth. For example, the surface can be adapted by being roughened, by being treated with an agent, compound or other chemical substance, by being pitted, by machining grooves, and by providing a hyaluronic acid biological surface coating.

The marker can be partially within the housing with a part of the marker outside the housing. The marker can be wholly enclosed by the housing.

The housing can be a single component or the housing can be made of multiple components. The housing can be made from any suitable bio-compatible material. the housing can be moulded about the marker. The multiple components of the housing can be joined using many methods, including brazing, welding and gluing with an adhesive. The component or components of the housing can be made of many materials, including metals, alloys, ceramics, plastics and combinations of the aforesaid.

The marker can be wirelessly detectable. Preferably the marker is wirelessly detectable using electromagnetic radiation, and most preferably using electromagnetic radiation within the radio frequency part of the electromagnetic spectrum.

The retaining formation can include a screw thread, a part of a screw thread, or a plurality of screw threads. The use of a screw thread facilitates both implantation and retention of the implantable marker in the bone.

The housing can have an insertion end which is tapered. The insertion end can provide a self-locating mechanism which facilitates locating the implantable marker in a hole. The insertion end can be bone penetrating. The insertion end can have a Trochar tip, or other tip which can penetrate bone. Hence the implantable marker can be pushed into the bone when a force is applied to the implantable marker. The insertion end can include a self taping screw thread. Hence, no hole is required in the bone and the implantable marker can be screwed directly into the bone. The insertion end includes a trochar tip alone or in combination with a self tapping thread or a tapered end.

The housing can have a connector for releasably engaging with an insertion tool. The connector can be any formation which allows a torque or rotational drive to be imparted to the implantable marker. For example, the connector can have a polygonal shape, non-circular curved shape, or can include a groove, lip, ridge, socket or other formation which can mate with a matching formation on the tool. The connector can be configured to prevent relative rotation between the implantable marker and an insertion tool, when connected to the insertion tool.

The housing or marker can include an attachment for receiving a thread, suture, wire or other thin, elongate element. Preferably the elongate element is flexible. The thin elongate element or suture can act as part of a re-location mechanism to aid removal of the implantable marker after it has been implanted.

The implantable marker can have an outer diameter of less than approximately 6 mm, preferably less than approximately 5 mm, more preferably less than approximately 4 mm and most preferably less than 3 mm. The implantable marker can have a diameter in the range of approximately 2 mm to 6 mm, preferably 2 mm to 5 mm, more preferably approximately 2 mm to 4 mm, and most preferably approximately 3 mm to 4 mm or 2 mm to 3 mm.

At least a first portion of the screw thread can have a cross section shaped to enhance retention of the implantable marker in the bone. At least a second portion of the thread can have a cross section shaped to enhance cutting into the bone. The cross section of the further portion of the thread can have a sharper profile than the cross section of the first portion of the thread. The first portion of the thread can have a cross section generally in the shape of a rounded trapezium.

The implantable marker can further comprise a transducer or sensor. The transducer or sensor can be for detecting a property in the region around the marker. Any property of the body providing useful information to a physician, clinician or surgeon can be detected. The property selected from the group comprising: pressure; temperature; biological activity; and chemical. The transducer or sensor can be provided within the housing and/or having at least a detector part exposed to the body.

According to a further aspect of the invention, there is provided a kit for percutaneously implanting an implantable marker in a bone. The kit can comprise a guide instrument, an insertion tool and/or an implantable marker. The guide instrument can have a guide channel extending at least partially along a longitudinal axis and can receiving an implantable marker. The insertion tool can be received within the channel of the guide and can translate at least partially along the longitudinal axis. The insertion tool can have a distal end for releasably engaging an implantable marker. The implantable marker can be received within the channel. The implantable marker can comprise a housing and a marker detectable by a tracking system in the housing. The insertion tool can be operable to drive the implantable marker into the bone.

The insertion tool can have an elongate body which includes a channel extending at least partially along the longitudinal axis of the elongate body for receiving a thread, suture, wire or other element, attached to the implantable marker.

The insertion tool can have an aperture for receiving the thread therethrough. The aperture can be located in a part of a connector for releasably attaching the implantable marker to the insertion tool. The aperture can be in communication with a bore which is in communication with a channel in the guide instrument.

A distal end of the guide instrument can have a bone engaging formation. The bone engaging formation can be adapted to penetrate at least partially into bone. The bone engaging formation can be adapted to resist rotation of the guide instrument about its longitudinal axis. The guide instrument can include a plurality of bone penetrating teeth. At least a first and a second of the plurality of bone penetrating teeth can face in opposite senses. Preferably at least two pairs of bone penetrating teeth are provided, facing in opposite directions.

The guide instrument can include a magazine for storing a plurality of implantable markers. The magazine can store a plurality of implantable marker and adaptor assemblies. The adapter can be releasable connectable to the drill. The assembly of the drill and adapter can provide an insertion tool. The adapter can include a connector at a distal end for releasably connecting to a proximal end of the implantable marker.

The magazine can include a dispensing mechanism configured to insert a further implantable marker into the guide channel after a current implantable marker has been implanted. The dispensing mechanism can be manually operable or automatically operable.

The kit can further comprise a drill receivable within the guide channel and translatable at least partially along the guide channel. The drill can have a drill bit at a distal end for creating a hole in the bone.

The kit can be assembled into an assembly. The assembly can include a skin piercing tip extending from a distal end of the guide instrument, so that the assembly can puncture the skin of a subject. The skin piercing tip can be a Trochar tip. The implantable marker can have the skin piercing tip. When the kit is assembled into the assembly the implantable marker can be located with the skin piercing tip extending from the distal end of the guide instrument. The kit can include a drill locatable within the guide channel and having a drill bit, and the drill bit can have the skin piercing tip. When the kit is assembled into the assembly the drill can be located with the skin piercing tip extending from the distal end of the guide instrument.

The insertion tool can be provided by an assembly of the drill and an adapter. The distal end of the insertion tool can be provided by a separable part or adapter into which at least the drill bit can be releasably fastened to provide the insertion tool.

According to a further aspect of the invention, there is provided a method for percutaneously implanting an implantable marker in a bone, the marker being detectable by a tracking system. The method can comprise puncturing the skin with an instrument.

The distal end of the instrument can be positioned adjacent the bone. The implantable marker can be driven into the bone from the instrument. The instrument can be withdrawn leaving the marker implanted within the bone. In this way surgical trauma can be reduced.

Driving the implantable marker into the bone can comprise pushing the implantable marker into the bone.

Driving the implantable marker into the bone can further comprise screwing the implantable marker into the bone.

The method can further comprise drilling a hole in the bone before driving the implantable marker into the bone. The implantable marker can be driven into the hole.

The instrument can include a guide channel extending at least partially along a longitudinal axis of the instrument and drilling the hole can include translating a drill at least partially along the guide channel of the instrument.

The implantable marker can have a skin piercing tip and puncturing the skin can include using the skin piercing tip of the implantable marker to puncture the skin.

The instrument can include a guide channel and a drill located within the guide channel, the drill can have a skin piercing tip, and puncturing the skin can include using the skin piercing tip of the drill to puncture the skin.

The implantable marker can have a thread, wire or other element attached to it which has a free end, and the method can further comprise leaving the free end of the thread outside the skin. Hence the thread or element can be used to facilitate removal of the implantable marker.

The method can further comprise using the thread to percutaneously guide a tool to engage with a free end of the implantable marker.

The method can further comprise using the tool to disengage the implantable marker from the bone and percutaneously withdrawing the marker from the bone so as to remove the implantable marker from the patient.

According to a further aspect of the invention, there is provided a method for tracking the position of a body part. The method can comprise percutaneously implanting an implantable marker in a bone using the method of the preceding aspect of the invention and tracking the position of the implantable marker using a tracking system.

The position of the implantable marker can be tracked wirelessly. The implantable marker can be tracked wirelessly using radio frequency electromagnetic signals.

According to a yet further aspect of the invention, there is provided a method for carrying out a computer aided or image guided surgical, prophylactic, medical or clinical procedure on a subject. The method can comprise carrying out a surgical, prophylactic, medical or clinical procedure and tracking the position of a body part of the subject during the surgical, prophylactic, medical or clinical procedure using the method according to the preceding aspect of the invention.

According to a further aspect of the invention, there is provided an implantable marker for percutaneously implanting within a bone. The implantable marker can comprise a housing having a body section, a distal end and a proximal end. The body section can be cylindrical and define a cavity therein. The distal end can be tapered and the proximal end can have a connector for engaging an insertion tool. The housing can have an outer surface bearing a screw thread. A marker can be enclosed within the cavity and be hermetically sealed and wirelessly detectable by a tracking system using radio frequency electromagnetic radiation. The implantable marker can be retained in the bone in use by the interaction of the screw thread and surrounding bone. The marker and cavity can be configured such that the marker is located within the surrounding bone when the implantable marker is implanted in the bone in use.

According to a further aspect of the invention, there is provided a guide for percutaneously implanting a device in a bone of a patient. The guide can include a guide tube and a housing attached to the guide tube. The housing can include a cartridge. The cartridge can include a plurality of bores or channels each for receiving a device to be implanted. The guide can further include a port for receiving an insertion instrument or tool in use to transfer a device from a bore into the guide tube. The guide can further include a mechanism for advancing the cartridge to a next bore. The cartridge can be substantially linear or substantially circular. The cartridge can be provided in the form of a drum rotatably mounted in the housing. The guide can include a switch, button or trigger actuable by a user to cause the cartridge to advance to a next bore.

Embodiments of the invention will now be described, by way of example only, and with reference to the accompanying drawings, in which:

FIG. 1 shows a schematic block diagram of a marker part of an implantable marker and a tracking system;

FIGS. 2A, 2B, 2C, 2D and 2E respectively show a perspective view, two longitudinal cross sectional views, a first end view and transverse cross sectional view of a housing part of an implantable marker according to the invention;

FIGS. 3A, 3B, 3C and 3D respectively show perspective, longitudinal cross sectional, side and longitudinal cross sectional views of an insertion guide instrument and parts thereof being a part of a kit according to the invention;

FIGS. 4A, 4B, 4C and 4D respectively show a perspective front, a perspective rear, a side, and a longitudinal cross sectional view of an insertion instrument being a part of a kit according to the invention;

FIG. 5 shows a perspective view of an end part of the insertion instrument in use with an implantable marker;

FIGS. 6A, 6B, 6C, 6D and 6E respectively show a perspective, side, distal end, proximal end and enlarged perspective view of the distal end of a drill part of a kit of according to the invention;

FIGS. 7A, 7B and 7C respectively show schematic cross section views of a bone having an implantable marker percutaneously implanted therein and illustrating a method according to the invention;

FIG. 8A shows a schematic perspective view of a further drill part, FIG. 8B shows a schematic perspective view of a further guide instrument part, and FIG. 8C shows a schematic perspective view of the end of the further drill and an assembly including an implantable marker and FIG. 8D shows a partial cross sectional diagram of the further drill and part of the assembly, all being parts of a further kit according to the invention;

FIG. 11 shows a flow chart illustrating a method for implanting the marker according to the invention in greater detail;

FIG. 13 shows a flow chart illustrating a method for removing the marker according to the invention in greater detail;

Figure 2A:
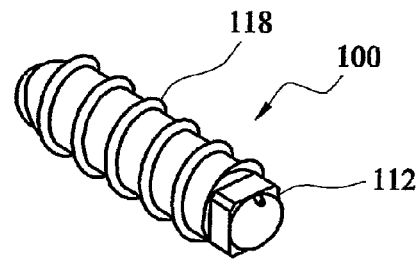

Similar items in different Figures share common reference numerals unless indicated otherwise.

Initially a suitable marker and associated tracking system will briefly be described. Aspects of the marker and tracking system are described in greater detail in U.S. patent publication no. US 2003/0120150 A1 (U.S. patent application Ser. No. 10/029,473, filed Dec. 21, 2001) which is incorporated herein by reference in its entirety for all purposes. However, it will be appreciated that other markers and tracking technologies can be used, including wired tracking systems, although wireless tracking technologies are preferred owing to their ease of use.

With reference to FIG. 1, there is shown a schematic block diagram of a magnetic tracking system 20. A marker of wireless position sensors 70 which can be tracked by the tracking system 20 is also shown. The marker generates and transmits signals that are indicative of its location and orientation coordinates, in response to an external magnetic field produced by a set of three field generator coils 32 (also referred to as radiator coils).

Field generator coils 32 are driven by driver circuits 34 to generate electromagnetic fields at different, respective sets of frequencies $\{w_1\}$, $\{w_2\}$ and $\{w_3\}$. Typically, the sets comprise frequencies in the approximate range of 100 Hz-20 kHz, although higher and lower frequencies may also be used. The sets of frequencies at which the coils radiate are set by a computer 36, which serves as the system controller for system 20. The respective sets of frequencies may all include the same frequencies, or they may include different frequencies. In any case, computer 36 controls circuits 34 according to a known multiplexing pattern, which provides that at any point in time, no more than one field generator coil is radiating at any given frequency. Typically, each driver circuit is controlled to scan cyclically over time through the frequencies in its respective set. Alternatively, each driver circuit may drive the respective coil 32 to radiate at multiple frequencies simultaneously.

For the purposes of system 20, coils 32 may be arranged in any convenient position and orientation, so long as they are fixed in respect to some reference frame, and so long as they are non-overlapping, that is, there are no two field generator coils with the exact, identical location and orientation. Typically, for surgical applications the coils are located in a triangular arrangement. The coil axes may be parallel, or they may alternatively be inclined. Bar-shaped transmitters or even triangular or square-shaped coils could also be useful for such applications.

In orthopedic and other surgical applications, it is desirable that coils 32 be positioned away from the surgical field, so as not to interfere with the surgeon's freedom of movement. On the other hand, the coils should be positioned so that the working volume of the tracking system includes the entire area in which the surgeon is operating. At the same time, the locations and orientations of coils 32 should be known relative to a given reference frame in order to permit the coordinates of tool implanted markers 70 to be determined in that reference frame. In practice, coils 32 are mounted on a reference structure.

The markers 70 include sensor coils 72, in which electrical currents are induced to flow in response to the magnetic fields produced by field generator coils 32. The sensor coils 72 may be wound on either air cores or cores of magnetic material. Typically, each marker comprises three sensor coils, having mutually orthogonal axes, one of which is conveniently aligned with the longitudinal axis of the housing of the implantable marker. The three coils may be concentrically wound on a single core, or alternatively, the coils may be non-concentrically wound on separate cores, and spaced along the longitudinal implantable marker. The use of non-concentric coils is described, for example, in the PCT Patent Publication WO 96/05768 and in the corresponding U.S. patent application Ser. No. 09/414,875 which are incorporated herein by reference in their entirety for all purposes.

Alternatively, the markers may each comprise only a single sensor coil or two sensor coils. Further alternatively, markers 70 may comprise magnetic position sensors based on sensing elements of other types known in the art, such as Hall effect sensors.

At any instant in time, the currents induced in the sensor coils comprise components at the specific frequencies in sets $\{w_1\}$, $\{w_2\}$ and $\{w_3\}$ generated by field generator coils 32. The respective amplitudes of these currents (or alternatively, of time-varying voltages that may be measured across the sensor coils) are dependent on the location and orientation of the marker relative to the locations and orientations of the field generator coils. In response to the induced currents or voltages, signal processing and transmitter circuits in each marker generate and transmit signals that are indicative of the location and orientation of the sensor. These signals are received by a receiving antenna 10, which is coupled to computer 36 via signal receiver and demodulation circuitry 12. The computer processes the received signals, together with a representation of the signals used to drive field generator coils 32, in order to calculate location and orientation coordinates of the implantable marker. The coordinates are used by the computer in driving a display 46, which can show the relative locations and orientations of the markers and other elements (such as prosthetic implants) to which similar markers have been fixed.

Although in FIG. 1, system 20 is shown as comprising three field generator coils 32, in other embodiments of the present invention, different numbers, types and configurations of field generators and sensors may used. A fixed frame of reference may be established, for example, using only two non-overlapping field generator coils to generate distinguishable magnetic fields. Two non-parallel sensor coils may be used to measure the magnetic field flux due to the field generator coils, in order to determine six location and orientation coordinates (X, Y, Z directions and pitch, yaw and roll orientations) of the sensor. Using three field generator coils and three sensor coils, however, tends to improve the accuracy and reliability of the position measurement.

Alternatively, if only a single sensor coil is used, computer 36 can still determine five position and orientation coordinates (X, Y, Z directions and pitch and yaw orientations). Specific features and functions of a single coil system (also referred to as a single axis system) are described in U.S. Pat. No. 6,484,118, whose disclosure is incorporated herein by reference.

When a metal or other magnetically-responsive article is brought into the vicinity of an object being tracked, the magnetic fields in this vicinity are distorted. There can be a substantial amount of conductive and permeable material in a surgical environment, including basic and ancillary equipment (operating tables, carts, movable lamps, etc.), as well as invasive surgery apparatus (scalpels, scissors, etc.). The magnetic fields produced by field generator coils 32 may generate eddy currents in such articles, and the eddy currents then cause a parasitic magnetic field to be radiated. Such parasitic fields and other types of distortion can lead to errors in determining the position of the object being tracked.

In order to alleviate this problem, the elements of tracking system 20 and other articles used in the vicinity of the tracking system are typically made of non-metallic materials when possible, or of metallic materials with low permeability and conductivity. In addition, computer 36 may be programmed to detect and compensate for the effects of metal objects in the vicinity of the surgical site. Exemplary methods for such detection and compensation are described in U.S. Pat. Nos. 6,147,480 and 6,373,240, as well as in U.S. patent application Ser. No. 10/448,289 filed May 29, 2003 and Ser. No. 10/632, 217 filed Jul. 31, 2003 which are all incorporated herein by reference.

Marker 70 in this embodiment comprises three sets of coils: sensor coils 72, power coils 74, and a communication coil 76. Alternatively, the functions of the power and communication coils may be combined, as described in U.S. patent application Ser. No. 10/029,473. Coils 72, 74 and 76 are coupled to electronic processing circuitry 78, which is mounted on a suitable substrate 80, such as a flexible printed circuit board (PCB). Details of the construction and operation of circuitry 78 are described in U.S. patent application Ser. No. 10/029,473 and in U.S. patent application Ser. No. 10/706,298, incorporated herein by reference.

Although for simplicity, FIG. 3A shows only a single sensor coil 72 and a single power coil 74, in practice sensor 70 typically comprises multiple coils of each type, such as three sensor coils and three power coils. The sensor coils are wound together, in mutually-orthogonal directions, on a sensor core 82, while the power coils are wound together, in mutually-orthogonal directions, on a power core 84. Alternatively, the sensor and power coils may be overlapped on the same core, as described, for example in U.S. patent application Ser. No. 10/754,751, filed Jan. 9, 2004, whose disclosure is incorporated herein by reference. It is generally desirable to separate the coils one from another by means of a dielectric layer (or by interleaving the power and sensor coils when a common core is used for both) in order to reduce parasitic capacitance between the coils.

In operation, power coils 74 serve as a power source for sensor 70. The power coils receive energy by inductive coupling from an external driving antenna 14 attached to RF power driving circuitry 16. Typically, the driving antenna radiates an intense electromagnetic field at a relatively high radio frequency (RF), such as in the range of 13.5 MHz. The driving field causes currents to flow in coils 74, which are rectified in order to power circuitry 78. Meanwhile, field generator coils 32 induce time-varying signal voltages to develop across sensor coils 72, as described above. Circuitry 78 senses the signal voltages, and generates output signals in response thereto. The output signals may be either analog or digital in form. Circuitry 78 drives communication coil 76 to transmit the output signals to receiving antenna 10 outside the patient's body. Typically, the output signals are transmitted at still higher radio frequencies, such as frequencies in the rage of 43 MHz or 915 MHz, using a frequency-modulation scheme, for example. Additionally or alternatively, coil 76 may be used to receive control signals, such as a clock signal, from a transmitting antenna (not shown) outside the patient's body.

Tracking system 20 also comprises RF power driver 16, which drives antenna 14 to emit a power signal, preferably in the 2-10 MHz range. The power signal causes a current to flow in power coil 74, which is rectified by circuitry 78 and used to power the markers internal circuits. Meanwhile, the electromagnetic fields produced by field generator coils 32 cause currents to flow in sensor coil 72. This current has frequency components at the same frequencies as the driving currents flowing through the generator coils. The current components are proportional to the strengths of the components of the respective magnetic fields produced by the generator coils in a direction parallel to the sensor coil axes. Thus, the amplitudes of the currents indicate the position and orientation of coil 46 relative to fixed generator coils 32.

Circuitry 78 measures the currents flowing in sensor coils 72 at the different field frequencies. It encodes this measurement in a high-frequency signal, which it then transmits back via antenna 76 to antenna 10. Circuitry 78 comprises a sampling circuit and analog/digital (A/D) converter, which digitizes the amplitude of the current flowing in sensor coils 72. In this case, circuitry generates an digitally-modulated signal, and RF-modulates the signal for transmission by antenna 76. Any suitable method of digital encoding and modulation may be used for this purpose. Other methods of signal processing and modulation will be apparent to those skilled in the art.

The digitally-modulated signal transmitted by antenna 76 is picked up by receiver 12, coupled to antenna 10. The receiver demodulates the signal to generate a suitable input to signal processing circuits in the computer system 36. Typically, receiver 12 amplifies, filters and digitizes the signals from marker 40. The digitized signals are received and used by the computer 36 to compute the position and orientation of marker 70. General-purpose computer 36 is programmed and equipped with appropriate input circuitry for processing the signals from receiver 12.

Preferably, the tracking system 20 includes a clock synchronization circuit 18, which is used to synchronize driver circuits 34 and RF power driver 16. The RF power driver can operate at a frequency that is an integer multiple of the driving frequencies of field generators 32. Circuitry 44 can then use the RF signal received by power coil 84 not only as its power source, but also as a frequency reference. Using this reference, circuitry 78 is able to apply phase-sensitive processing to the current signals generated by sensor coils 72, to detect the sensor coil currents in phase with the driving fields generated by coils 32. Receiver 12 can apply phase-sensitive processing methods, as are known in the art, in a similar manner, using the input from clock synchronization circuit 18. Such phase-sensitive detection methods enable marker 40 to achieve an enhanced signal/noise (S/N) ratio, despite the low amplitude of the current signals in sensor coils 72.

Although certain frequency ranges are cited above by way of example, those skilled in the art will appreciate that other frequency ranges may be used for the same purposes.

Circuitry 78 also stores a unique identifier for marker 70 and the unique identifier is also transmitted to the tracking system 20, so that the tracking system can determine the identity of the marker from which positional data is being received. Hence the tracking system can discriminate between different markers when multiple markers are present in the working volume of the tracking system.

An advantage of using wireless markers, such as marker 70, without an on-board power source, is that the markers can be inserted in and then left inside the patient's body for later reference.

As illustrated in FIG. 1, the marker 70 is hermetically sealed by encapsulation in a sealant or encapsulant 86. Preferably the sealant provides any, some or all of the following shielding properties: mechanical shock isolation; electromagnetic isolation; biocompatibility shielding. The sealant can also help to bond the electronic components of the marker together. Suitable sealants, or encapsulants, include USP Class 6 epoxies, such as that sold under the trade name Parylene. Other suitable sealants include epoxy resins, silicon rubbers, and polyurethane glues. The marker can be encapsulated by dipping the marker in the sealant in a liquid state and then leaving the sealant to set or cure.

With reference to FIGS. 2A to 2E there is shown a housing part 100 of an implantable marker according to the present invention. Housing 100 has a generally right cylindrical body portion 102 with a distal end 104 and a proximal end 106. The housing 100 has a cavity 108 defined therein for receiving an encapsulated marker 40 to provide the implantable marker.

The distal end 104 has a generally tapered shape and includes a tip 110 for self-locating the implantable marker in a hole in a bone in use as will be described in greater detail below.

The proximal end 106 of the housing has a substantially square shaped formation 112 which provides a connector for releasably engaging with an insertion tool as will be described in greater detail below. The proximal end 106 has a bore 114 passing there through for receiving a thread or suture which can assist in removal of the implantable marker as will also be described in greater detail below. It will be appreciated that the connector formation 112 can have other shapes which allow an instrument to be releasably connected thereto so as to impart rotational drive to the implantable marker. For example the connector can have any polygonal shape, such as triangular or star shaped, and can also have a curve shape, such as an oval or elliptical shape. In alternate embodiments, the connector can also be in the form of a slot, rib or lip for engaging with a matching connector formation on the end of insertion tool. As illustrated in FIG. 2a, the corners of the connector formation 112 are preferably chaffered in order to facilitate engagement of the connector and insertion tool.

The self-locating tip 110 can be provided as an integral part of housing 100 or can be provided as a separate part which is subsequently attached to housing 100. For example tip 110 can be moulded on to the distal end 114 of housing 100, mechanically fixed thereto or attached using an adhesive or any other suitable techniques, depending on the materials of the tip 110 and distal end 104 of housing 100. Tip 110 can be made of a resorbable material so that the tip is resorbed into the bone of a patient over time. Bioresorbable materials includes any suitable materials that will break up and disappear within the body. In one embodiment, the resorbable material is polylactic acid although other resorbable materials can be used e.g. Polyglycolic acid, caprolactone, ethylene oxide polymers, and similar. In some embodiments, the tip can be made of a biodegradable material such as Polypropylene. Biodegradable materials includes any suitable material that can break up and reside as another material within the body.

Housing 100 has an outer surface 116. A screw thread 118 is provided on the outer surface and extends along substantially the entire length of the housing body. Screw thread 118 interacts with surrounding bone in use to anchor the implantable marker in the bone material so as to retain the implantable marker securely in place when implanted.

Figure 2B:
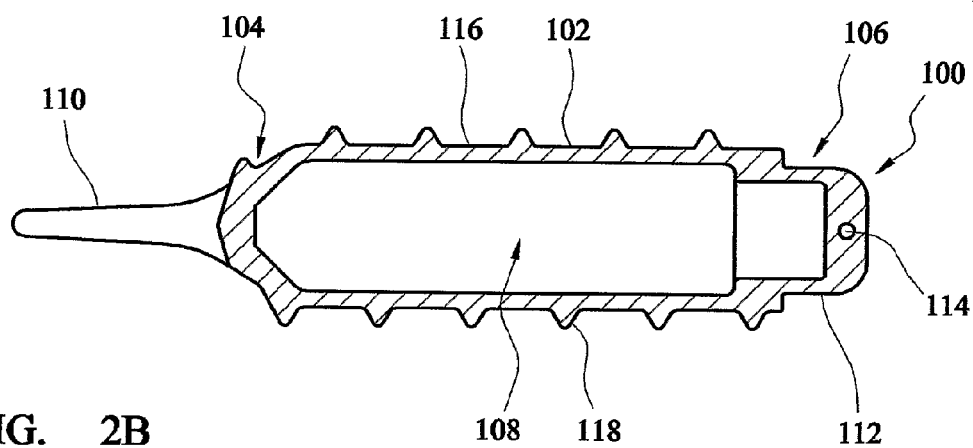
Figure 2C:
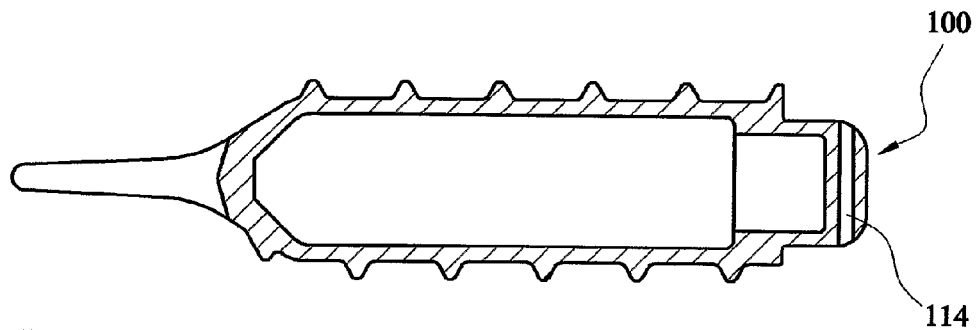
Figure 2D:
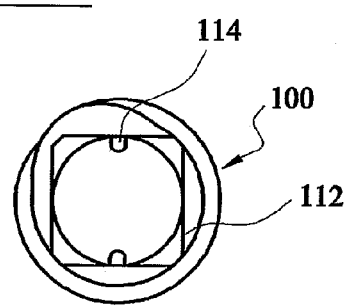
Figure 2E:
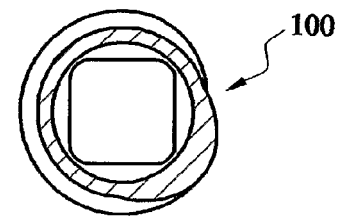

In one embodiment, the profile of the thread is selected so as to be not too sharp and not too blunt. It has been found that too sharp a thread profile, while providing a good cutting action into the bone, can cause the bone to resorb from the thread thereby reducing the retention of the implant in the bone. A blunter thread profile does not provide as good a cutting action as a sharper profile, but provides improved retention of the implant in the bone, as the surrounding bone has a reduced tendency to retreat from the more rounded thread. As best illustrated in FIGS. 2b and 2c, which show cross sections along the longitudinal axis of the housing 100, the cross sectional shape or profile of the thread has a rounded or flattened apex and can be considered to have a generally rounded trapezoidal cross section. In one embodiment, the radius of curvature where the thread joins the body can be of order 100 microns. In one embodiment, the thread profile can vary along the length of the body. The thread can have a sharper profile toward the distal end of the housing so as to provide a good initial cutting action. The thread profile towards the proximal end of the housing can have a more rounded, flatter profile, so as to provide a better anchoring mechanism. The thread profile can vary continuously along the longitudinal axis of the housing or alternatively, can vary discretely and multiple different thread profiles can be provided in order to balance the requirements of a good cutting action and good anchoring and retention of the implantable marker.

The housing 100 can be made of a variety of materials and can be constructed in a variety of ways. In one embodiment, the housing is made of an X-ray opaque material so that the implantable marker will be easily identifiable in X-ray images. It is also preferred if the material of the housing is easily visualisable in CT and/or MRI scan images. The housing can be made of ceramic materials, e.g. zirconium, alumina or quartz. The housing can be made of metals, e.g. titanium and other bio-compatible metals. The housing can be made of alloys, e.g. $Ti_6Al_4V$. The housing can be made of plastics materials, e.g. epoxy resins, PEEKs, polyurethanes and similar. Also, the housing can be made of combinations of the above materials and the housing can be made of component parts made of different types of materials, selected from the above mentioned materials at least. The component parts can be joined together using any suitable technique, such as brazing, welding or by using suitable glues or adhesives.

In one preferred construction, the housing is assembled from three elements, in which the distal end 104 is in the form of a titanium cap, a portion of the body 102 is in the form of a titanium collar and the proximal end 106 is in the form of a ceramic end cap. The titanium collar is joined to the ceramic proximal end portion by brazing, the encapsulated marker is inserted within the body and finally the distal end cap is assembled over the end of the marker and laser welded to the titanium collar. The marker is positioned with the RF power antenna toward the proximal end and the sensor coils toward the distal end of the housing.

In another embodiment, the housing is made from two ceramic parts which are then laser welded together along a joint extending along the longitudinal axis of the housing. In other embodiments, the housing can be provided by moulding the housing around the encapsulated marker for example by moulding a plastics material around the marker. The internal shape of the mould can be used to define the outer shape of the housing. Alternatively, the outer shape of the housing can be defined by subsequently machining the material moulded around the marker.

Housing 100 wholly encloses the marker and further hermetically seals the encapsulated marker. It is preferred if a small volume, e.g. approximately 1 $mm^3$ of air is provided as free space in the hermetically sealed housing so as to allow for expansion owing to changes in temperature. It is also preferred to include a small amount, e.g. 1 $mm^3$ of hygroscopic material to absorb moisture from the internal atmosphere of the housing. Suitable materials include MgS and silica gel.

In one embodiment, the marker has a diameter of approximately 4.5 mm (thread to thread) and the collar has an external diameter of approximately 3.6 mm (outer surface to outer surface. The internal diameter of the collar can be approximately 3 mm and the walls of the collar can be approximately 0.3 mm. The interior of the housing can be approximately 10 mm long and the overall length of the housing (omitting any nose 110) can be approximately 14 mm.

In the embodiment illustrated in FIGS. 2A to 2E, the thread 118 provides a bone anchor. The bone anchor can be provided by other mechanisms. The bone anchor can be provided by other formations on the surface of the housing. The bone anchor can also be provided by the surface of the housing and/or the surface of any formations on the housing, by suitably treating or otherwise configuring the surface of the housing so as to promote bone on growth on to the outer surface and/or formations of the housing. Examples of bone anchor formations, include screw threads, barbs, ridges, ribs and other large scale formations which can be provided on the outer surface of the housing.

In other embodiments, a rough outer surface can provide a bone anchor and a rough outer surface can be realised by using a mould having a roughened inner surface so that the outer surface of the moulded housing is roughened. In other embodiments, the surface finish of the housing can be used to provide a bone anchor e.g. by blasting the surface with titanium to provide approximately 12 micron roughness. The material with which the surface of the housing is blasted can vary and is typically the same material as the material of which the housing is made. For example a ceramics housing can be blasted with ceramics materials to provide enhanced roughness to promote or otherwise facilitate bone on growth.

In another embodiment, the surface of the housing can be treated to promote bone on growth by sintering small balls or particles of material on to the outer surface of the housing. For example, balls of approximately 250 micron diameter metal particles can be sintered to the outer surface of the housing. Such a surface coating is provided under the trade name Porocoat by DePuy International Limited of Leeds, the United Kingdom. In other embodiments, a mesh can be provided on the outer surface of the housing to promote bone on growth. In other embodiments, a hydroxy apatite coating can be provided on the outer surface of the housing. Other forms of coating can also be provided so as to promote or otherwise facilitate bone on growth.

Figure 9:
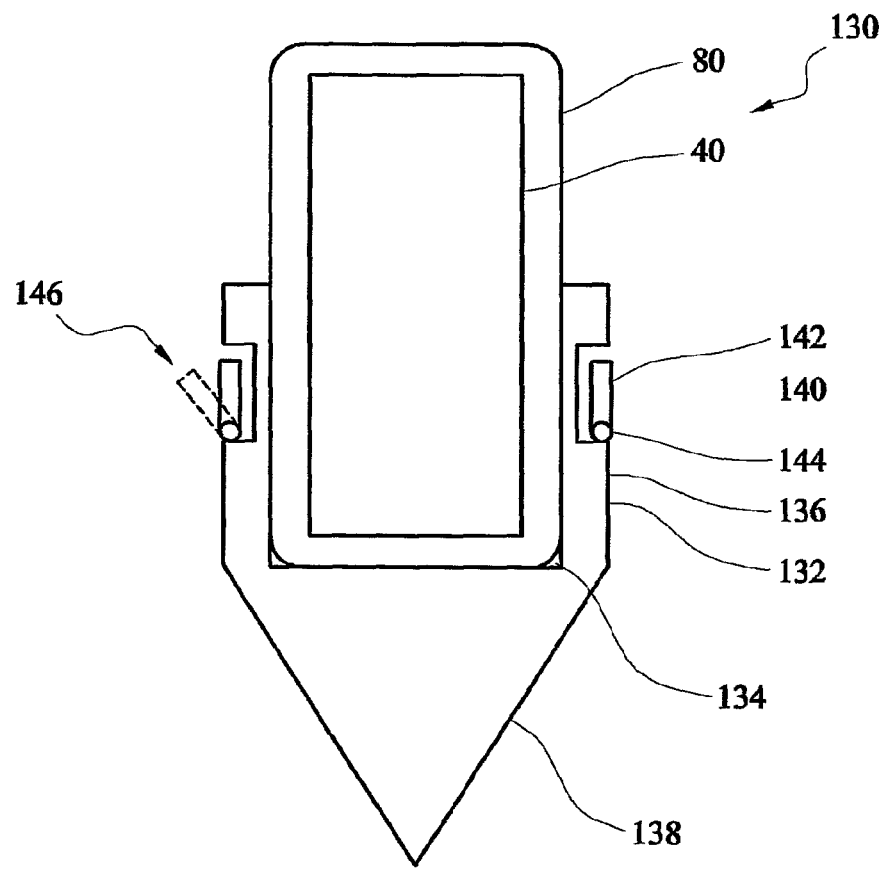
FIG. 9 shows a schematic cross sectional diagram of a further implantable marker according to the invention.

With reference to FIG. 9 there is shown a schematic cross section of a further embodiment of an implantable marker 130. In this further embodiment, the implantable marker comprises encapsulated marker 70 and housing 132. Encapsulated marker 70 is secured within a cavity 134 defined by a body part 136 of housing 132. A distal end 138 of the housing 132 is provided in the form of a self-cutting, bone penetrating tip which is sufficiently sharp to cut through soft tissue and penetrate into bone. The self-cutting tip 138 can be in the form of a Trochar or other sharp shape capable of penetrating bone.

The encapsulated marker is not wholly enclosed in this embodiment and a part of the marker, including the power coil and antenna is exposed. The sensor coil part of the marker is located within the cavity of the housing. This way, when the implantable marker is implanted within a bone, the sensing coils 42 are located within the bone and surrounded by bone so that the position indicated by the sensing coils corresponds to a position within the bone adjacent to the surface of the bone.

Implantable marker 130 has a bone anchor in the form of a plurality of barbs 140 located around the periphery of the housing 132. Each barb is in the form of a rigid member 142 mounted by a pivot 144 to the body of the housing. Pivot 144 includes a spring, or other resilient biasing means, which biases the member 142 away from the stowed state illustrated in FIG. 9 and toward a deployed state as illustrated by dashed lines 146. In the deployed state, the element 142 acts as a barb which resists movement of the housing out of the bone so as to retain the implantable marker within the bone. Bone anchor 140 can be provided in other forms. For example the bone anchor can be provided as a continuous part of housing 132, in the form of a leaf spring which is biased towards the deployed state so as to act as a barb. Alternatively, the bone anchor can be in the form of teeth, serrations or other barbed formations on the outer surface of housing 132 which are permanently in a "deployed" state and which do not have a stowed state.

The implantable marker 130 is particularly suited for use in a "push fit" insertion method as will be described in greater detail below.

Figure 10:
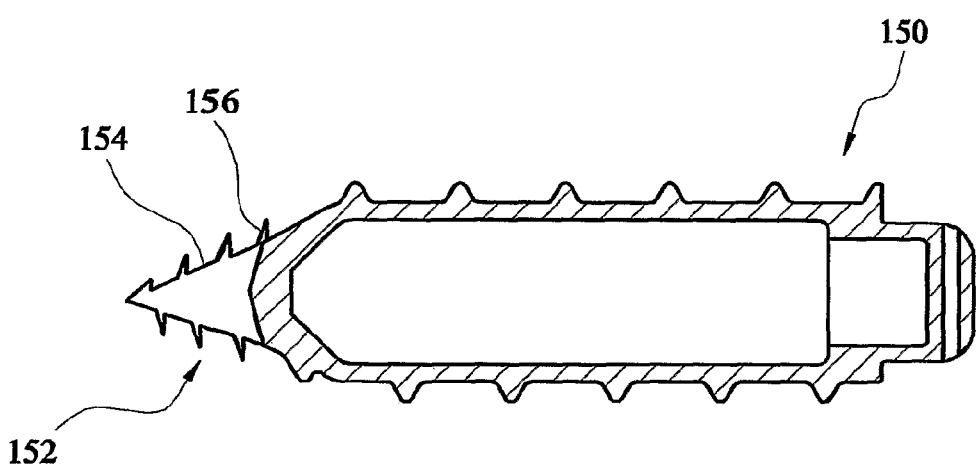
FIG. 10 shows a schematic longitudinal cross sectional diagram of a further housing part of an implantable marker according to the invention.

With reference to FIG. 10, there is shown a further embodiment of an implantable marker 150. Implantable marker 150 has a housing similar to that shown in FIGS. 2a to 2e, but the distal end 152 has a tip 154 bearing a self-tapping screw thread 156. Self-tapping screw thread 156 allows this embodiment of the implantable marker to be used in a self-tapping implantation method as will be described in greater detail below.

A set of instruments particularly suitable for use in percutaneously implanting the first embodiment of the implantable marker will now be described in greater detail with reference to FIGS. 3 to 6.

FIG. 3A shows an exploded perspective view of a guide instrument 160. The guide instrument 160 includes a plastics handle 162 and an elongate cylindrical body 164 having a guide channel 166 extending along the longitudinal axis thereof. The guide body can be in the form of a tube of bio-compatible metal, such as stainless steel, titanium or other suitable metals or alloys. The guide body has a first aperture at a proximal end 168 and a second aperture in a distal end 170. The distal end has two pairs of teeth arranged in diametrically opposed fashion. Each pair of teeth, or barbs, is arranged in a different sense of orientation with respect to the other pair. The teeth are sufficiently sharp that under a load of up to 10 kg, the teeth will penetrate into bone so as to reliably locate the guide. The opposed sense of the teeth and their barbed shape helps to prevent rotation of the guide relative to the bone. The guide body 164 includes a threaded portion 172 which cooperates with an interior threaded portion of handle 162 whereby the handle 162 is attached to the guide body 164. The outer surface 174 of guide tube 164 can be highly polished or otherwise treated to have a low coefficient of friction so as to facilitate penetration of the guide through the skin in use. Each tooth is approximately 1 mm long and the internal diameter of the guide channel 166 is approximately 3 mm.

With reference to FIGS. 4A to 4D, there are shown various views of an insertion instrument 180. The insertion instrument has a generally linear elongate body 182 having a distal end 184 and a proximal end 186. Proximal end 186 has a generally triangular cross sectional shape and provides a coupling by which a power tool can be releasably connected to the insertion tool so as to impart talk or rotational drive to the insertion tool 180. Other coupling formations can be used in place of the triangular coupling formation illustrated in the figures. The distal end 184 of the insertion tool 180 includes a connector 190 for releasably engaging with the proximal end 106 of the implantable marker 100. The connector 190 includes a generally square shaped aperture adapted to engage and mate with the square shaped connector formation 112 of the implantable marker 100. A channel 194 is provided to out an outer surface of the insertion tool and extends along the longitudinal axis of the insertion tool. A distal end of channel 194 merges with a bore 196 extending between the channel 194 and an aperture 198 located within the square recess 192.

As illustrated in FIG. 5, in use, a thread or suture can be passed through channel 114 in the proximal end of the implantable marker and the thread 200 is passed through bore 196 via aperture 198 and can lie in channel 194 with a free end of thread 200 trailing off the proximal end 186 of the insertion tool. The thread 200 can subsequently be used to facilitate removal of an implanted implantable marker as will be described in greater detail below. The interaction of the thread, insertion tool connector and implantable marker 100 is best illustrated by FIG. 5.

With reference to FIGS. 6A to 6E there are shown various views of a drill part which can be provided as part of a kit of instruments according to the invention. Drill 204 has a generally solid cylindrical elongate body 206 with a drill bit 208 at a distal end and a connector 210 at a proximal end. A collar 212 separates the connector from the body 206. Drill bit 208 has a skin penetrating tip 214 which can be in the form of a Trochar as best illustrated in FIGS. 6c and 6e. Connector 210 has a generally triangular cross sectional shape and provides a releasable connector by which a power tool can be connected to the drill to impart talk or rotational drive to the drill. Drill 204 can be used with the guide depending on the nature of the implantable marker to be implanted. Typically, drill 204 is used when the implantable marker does not have a self-cutting tip as will be described in greater detail below. Drill 204 and insertion tool 180 are both made from a suitable bio-compatible material, such as titanium or stainless steel.

A method for percutaneously implanting the implantable marker in the bone of a patient using the previously described instruments will now be described with reference to FIGS. 7A to 7C. With reference to FIGS. 7A to 7C there is illustrated a method for implanting an implantable marker into the bone of a subject through the skin of a subject using instruments similar to those described previously. FIG. 7A shows a part 220 of the body of a subject, e.g. the thigh, including the skin 222 and the bone 224, in this example a part of the femur. Use of the method is not restricted to the femur and the method can be used to implant a marker into any bone.

Initially, drill 204 is inserted into the guide channel of guide instrument 160 with at least the tip 214 of the drill exposed beyond the distal end of guide 160 from aperture 170. With the drill and guide assembled in this manner, the distal end of the assembly is placed on the skin above the site at which the implant is to be implanted and a force is applied to the assembly. The tip 214 of the drill punctures the skin and the assembly is pushed through the skin until the drill tip 214 and teeth of the guide tool engage the bone 224. The drill 204 can slide within the guide channel 166 and so both the drill tip 214 and teeth can be brought into engagement with the outer surface of bone 224. A further force can be applied to handle 162 of the guide so as to cause the teeth to penetrate into the bone thereby reliably retaining the guide in position and so as to prevent rotation of the guide.

A power tool can then be attached to the connector 210 of the drill to impart rotational motion and the drill can be driven into the bone 224 so as to drill an initial hole 226 into the bone 224. FIG. 7A illustrates the drill 204 being rotated to drill hole 226 in the bone.

The drill 204 can then be withdrawn from the guide channel 166 in the guide instrument 160. An implantable marker is connected to the end of an insertion tool 180 with thread 200 passing along bore 196 and being located in channel 194. Then, as illustrated in FIG. 7b, the insertion tool and implantable marker assembly is inserted into the guide channel and moved toward hole 226 in the bone 224. Hence the implantable marker 100 is passed through the skin 222 in order to be implanted. Tip 110 of the implant helps to automatically locate and centre the implantable marker in hole 226. A power tool or manual tool is then connected to the connector 186 on the proximal end of the insertion tool and the insertion tool is rotated so as to drive implantable marker 100 into the bone 224 thereby driving the implantable marker 100 into the bone 224.

The screw thread 118 anchors the implantable marker in the bone and the insertion tool is withdrawn from the guide channel and the implanted marker and insertion tool connectors disengage and the thread 200 is paid out as the insertion tool is removed. The guide 160 is then withdrawn as illustrated in FIG. 7C, leaving the implantable marker implanted in the bone 224 and also leaving the thread 200 attached at one end to the implantable marker and having a free end located above the skin 222. It will be appreciated that both the insertion tool and guide tool can be withdrawn simultaneously as well. The guide tool helps to protect the implant as it is introduced into the bone through the skin.

As illustrated in FIG. 7C, when the implantable marker is implanted, the marker is located within the surrounding bone 224, rather than standing proud of the bone, e.g. on a support structure. Therefore the position of the marker within the implantable marker more accurately reflects the position of the bone. Also, as the marker is effectively injected through the skin of the subject, there is no need to use ancillary incisions in order to attach the marker to the bone thereby reducing trauma. Only a single simple procedure needs to be used to used to implant the marker and that procedure is much simpler than a surgical intervention. Hence there are a number of benefits associated with this percutaneous approach to implanting a marker.

The marker is itself hermetically sealed and the housing can be further hermetically sealed, and so the marker can be left in the patient for a significant period of time, e.g. 25 years. Therefore, the marker of the present invention is particularly suited for use in monitoring the long term behaviour of a patient's bones.

In order to remove the implantable marker, the free end of the thread 200 is passed through the bore 196 in the insertion instrument and used to guide the distal end of the insertion tool as it is pushed through the skin 222 until the connector 190 engages with the connector 112 of the implantable marker 100. The thread 200 is held under tension and the insertion tool is rotated so as to withdraw the implantable marker 100 from the bone 224 by unscrewing it. The insertion tool and implantable marker are gradually withdrawn as the implantable marker is released from the bone until the implantable marker is free of the bone at which time the insertion tool and implantable marker assembly can be withdrawn through the skin. Hence, the thread cooperates with the insertion tool to provide a reliable mechanism for relocating the implantable marker and disengaging the implantable marker from the bone.

Slightly different implantation methods can be used for the implantable markers shown in FIGS. 9 and 10.

Implantable marker 130 can be inserted directly into the bone and does not require a pre-drilled hole. Hence, drill 204 is not required and insertion tool 180 is adapted to include a connector which can releasably engage with a proximal portion of implantable marker 130. For example, a suitable, releasable engagement mechanism would be a bayonet type fitting. Hence, in order to implant implantable marker 130 through the patient's skin, the implantable marker is connected to the distal end of the insertion tool and the insertion tool and marker assembly is inserted into the guide channel of guide 160 with the tip 138 of marker 130 extending beyond the distal end of the guide. The tip 138 of the marker is used to puncture the skin and the assembly of the guide, insertion tool and marker is passed through the skin with the guide protecting the parts of the marker located within the guide channel. The teeth of the guide can be pushed into the bone to reliably locate the guide and then a force is applied to the proximal end of the insertion tool and the implantable marker can be driven into the bone of the patient owing to the bone penetrating tip 138.

When the implantable marker has been pushed a sufficient distance into the bone, the bone anchors 140 are urged outwardly to engage with surrounding bone to help retain the implantable marker within the bone. Owing to the configuration of the cavity and position of the marker within the cavity, the sense coils of the marker are located substantially within the surrounding bone towards the upper surface of the bone thereby providing an accurate indication of the position of the bone of the patient.

The insertion tool can then be released from the implantable marker and the insertion tool and guide withdrawn, leaving the implantable marker in place. Hence, in this embodiment, the implantable marker is a self-cutting implantable marker which can be driven into the bone without requiring a pre-drilled hole.

The implantable marker 150 illustrated in FIG. 10 also does not require a pre-drilled hole and so can be implanted without the use of drill 204. Implantation of implantable marker 150 is similar to that of implantable marker 130 in that assembly of insertion tool 180 and implantable marker 150 is introduced into guide instrument 160 with the tip of the implantable marker 150 exposed at the distal end of the guide instrument. The tip of the implantable marker is used to puncture the skin and the assembly of guide, implantable marker and insertion tool is pushed through the patient's skin. The implantable marker 150 is then screwed into the bone using the self-tapping thread of the tip until the implantable marker has been screwed into the bone and is retained therein when the guide and insertion tool are removed. Removal of implantable marker 150 is similar to the removal of implantable marker 100 as described above.

With reference to FIGS. 8A to 8D, there is shown a further embodiment of a set of instruments and an implantable marker similar to those described above. FIG. 8A shows a drill 250 having a drill bit 252 with a skin piercing tip 254 at a distal end. Drill body 256 has a threaded portion 258 between the drill bit 252 and the remainder of the body of the drill. Drill 250 also has a channel 260 in an outer part of the drill and extending along the longitudinal axis of the drill. Channel 260 is for receiving a thread 200 similar to channel 194 in insertion tool 180. A connector 262 is provided to a proximal end of the drill and is similar to connector 186 of insertion tool 180. A collar 264 with channel 260 passing there through is provided between the connector and body part 256 of the drill.

With reference to FIG. 8D in particular, there is shown the distal part of the drill 250 and an adapter part 270. Adapter 270 is releasably connectable to the distal end of drill 250 such that the combination or assembly of drill 250 and adapter 270 provides an insertion tool similar to insertion tool 180. The adapter body defines a cavity 271 therein generally shaped to match the shape of the distal end of the drill and including a portion for receiving the drill bit 272 and having a portion bearing an internal thread 274. The threaded portion 258 of drill 250 co-operates with the threaded portion 274 of adapter 270 to connect the adapter to the drill. The distal end of adapter 270 includes a generally square shaped recess 192 similar to that at the end of insertion tool 180 and also including a bore (not shown) for receiving thread 200 in use. Hence, when drill 250 and adapter 270 are connected, the drill and adapter assembly provides an insertion tool similar to that shown in FIG. 180.

With reference to FIG. 8B, there is shown a further embodiment of a guide instrument 300. Guide instrument 300 is generally similar to guide instrument 160 except that handle 302 is adapted to receive a magazine 304 which can hold a plurality of implantable marker-adapter assemblies 306.

As illustrated in FIG. 8C, the implantable marker 290 and adapter 270 assembly 306 comprises an implantable marker similar to that shown in FIGS. 2A-2E, but with a thread extending along the tip. Thread 308 is spooled around the outer surface of adapter 270 and can be unwound therefrom after implantation of the implantable marker.

Magazine 304 holds a plurality of assemblies 306 and includes a drive mechanism to advance a next of the assemblies into a breach portion 310 of the guide instrument 300 after a previous assembly has been implanted and after the drill 250 has been removed. A spring or other biasing means is provided within magazine 304 to urge assemblies sequentially into the breach area 310.

The method of using guide instrument 300 to implant multiple implantable markers is similar to that described previously but differs in the following respects. Initially, the drill 250 is located within the guide channel of the guide instrument 300 with the tip of the drill 254 exposed at the distal end of the guide instrument. The guide instrument and drill assembly is pushed through the skin and the teeth of the guide are pushed into engagement with the bone. The drill 250 is operated to drill a hole in the bone and then the drill is withdrawn from the guide channel and a first marker and adapter assembly 306 is automatically fed into the breach region 310. The distal end of drill 250 is then inserted in cavity 271 via the proximal end of the adapter 370 and the drill is screwed into engagement with adapter 270 such that they are locked together. The drill, adapter, implantable marker assembly is then translated along the guide channel and the implantable marker is then screwed into the previously drilled hole. The sense of the thread on the implantable marker should be the same sense as the threaded part 258 of drill 250 to ensure that drill 250 does not disengage from adapter 270. After the implantable marker 290 has been driven into the bone and has passed out from the distal end of the guide tube, the adapter and drill are withdrawn as a single unit and the thread 308 is unraveled from the outer surface of the adapter 270.

The drill and adapter 270 are then removed from the guide instrument and the adapter 270 can be unscrewed from the end of drill 250 and disposed of. The guide instrument can then be withdrawn through the skin or alternatively the guide instrument and drill-adapter assembly can be withdrawn together. After the first adapter 270 has been dispensed with, the drill 250 is reintroduced into the guide instrument 300 and the guide instrument is then inserted into another region of skin in order to implant a further implantable marker. A manually actuable button or trigger can be used to advance the magazine 304 in order to introduce a further marker-adapter assembly 306 into the breach region 310 after a hole has been drilled and the drill 250 has been removed from the breach region 310.

With reference to FIG. 11, there is shown a flowchart illustrating an embodiment of the method 320 for percutaneously implanting an implantable marker according to an aspect of the invention. FIGS. 12A to 12D show the instruments and tools being used in the percutaneous implantation method 320.

Figure 12A:
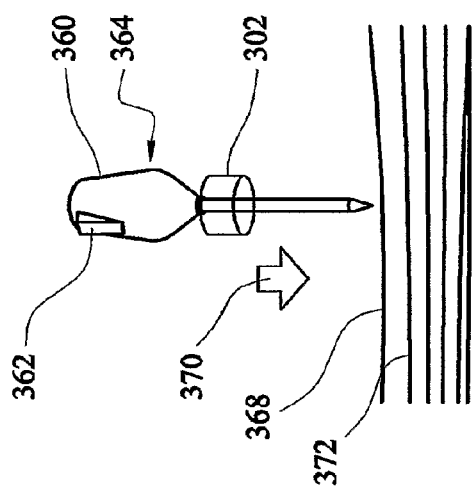
FIGS. 12A to 12D illustrate the instruments of the invention being used in the method illustrated by FIG. 11.

FIG. 12A shows the distal end of the drill instrument extending from a distal end of the guide tube in greater detail. A drive mechanism 360 is attached to a proximal end of the drill and includes a powered drive, e.g. electrical motor, and a switch or button 362 operable by a user to impart rotational motion, in either direction to the body of the drill.

At step 322, the instrument assembly 364 is pushed through the skin 368 of the patient by a user pushing on the instrument assembly in the direction indicated by arrow 370. The skin piercing tip of the drill bit penetrates the outer surface of the skin and allows the drill and guide tube to be inserted through the patient's skin. The drill can move in the guide channel relative to the guide tube and the guide tube is pushed towards the bone until the distal end of the guide tube engages with the outer surface of the bone 372 of the patient. The distal end of the guide tube bears teeth or other serrated formations which can be pushed into the bone so as to reliably position the guide tube and so as to prevent rotation of the guide tube.

Figure 12B:
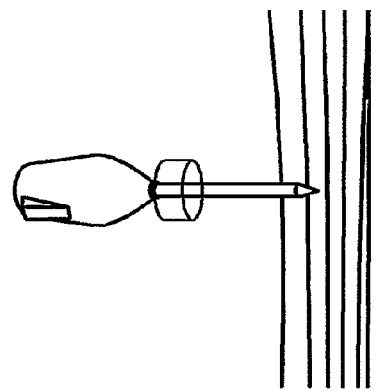
Figure 12C:
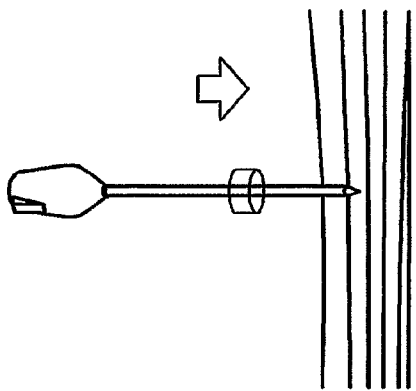

Then at step 324, as illustrated in FIG. 12B, a hole is drilled in the bone 372 by the user operating switch 362. Then at step 326, after a hole has been drilled in the bone, the drill is withdrawn along the guide tube until the drill bit is located within housing 302 of the guide instrument. This configuration of the instrument assembly 364 is illustrated in FIG. 12C. FIG. 12C shows an enlarged view of housing 302 and the body of drill instrument extending therefrom. Within housing 302, there is provided the cartridge, or magazine, including a plurality of implantable markers. In one embodiment, the drill instrument is removed from the housing 302 and an adapter, or connector 270, is attached over the end of the drill bit. The adapter has an end with a square recess therein for releasably engaging with the connector of the implantable marker housing. With the adapter attached over the drill bit, an insertion tool is provided. In alternate embodiment, a separate insertion tool is provided. In a further alternate embodiment, a plurality of assemblies of implantable markers and prospective adapters are provided in housing 284.

Figure 12D:
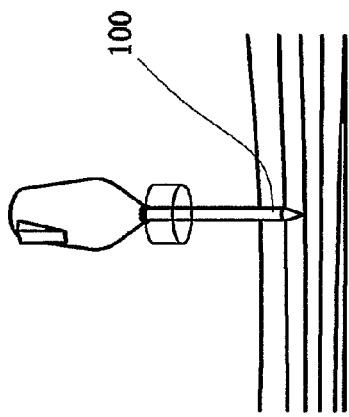

Irrespective of whether a separate insertion tool is provided or whether the adapter and drill provide the insertion tool, at step 328, the end of the insertion tool/adapter is engaged with a one of the implantable markers in housing 302. FIG. 12C shows an enlarged view of the distal end of the insertion tool/adapter with the implantable marker releasably connected thereto. The insertion tool is pushed along the guide channel of the guide instrument as indicated by arrow 370 and the implantable marker is driven into the pre-drilled hole at step 330 by the user pressing the button 362. In an alternate embodiment, the implantable marker can be manually screwed into the pre-drilled hole. FIG. 12D illustrates the implantable marker 200 having been percutaneously implanted within a cortical region of bone 372.

At step 332, the instrument assembly is withdrawn from the patient's skin. At 334, the user can then percutaneously implant a further implantable marker if required, in the same manner, as indicated by line 336. For example, a first implantable marker may be implanted in the tibia and a second implantable marker may be implanted in the femur, so as to allow the positions of the tibia and fibia to be tracked during a computer aided surgical procedure. If it is determined at step 334 that no further implantable markers are required in the patient's bones, then the method ceases at step 338.

Figure 14B:
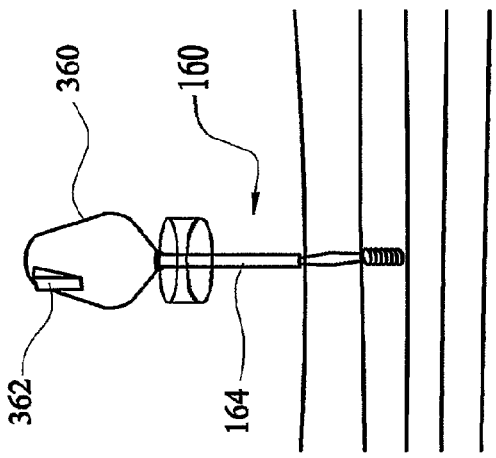
FIGS. 14A to 14D illustrate the instruments of the invention being used in the method illustrated by FIG. 13.
Figure 14A:
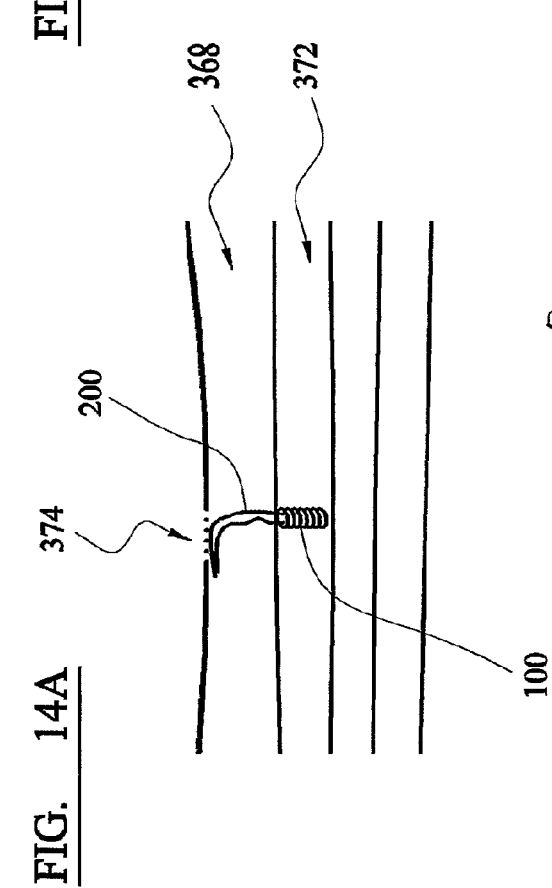
Figure 14D:
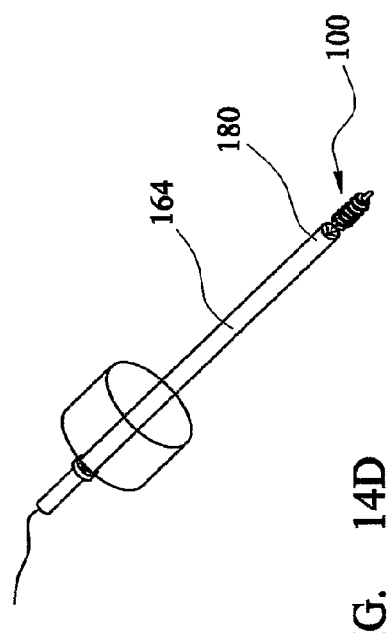

With reference to FIG. 13, there is shown a flow chart illustrating the method 340 for removing an implanted implantable marker from the bone 372 of a patient through the patient's skin 368 in greater detail. Steps of the method are illustrated in FIGS. 14A to 14D. As illustrated in FIG. 14A, the implantable marker can have a length of suture 200 passing through channel 114 in the proximal end of the implantable marker housing. The length of suture can be used to close the point in the skin where the implantation instruments puncture the skin's surface. Stitches 374 in the skin 300 of the patient therefore approximately indicates the location of the implantable marker 100 in the bone 372.

Method 340 begins at step 342 and initially a user of the method locates the approximate position of the implantable bone marker at step 344. The stitches 374 are undone and the ends of the suture 200 are obtained.

Figure 14C:
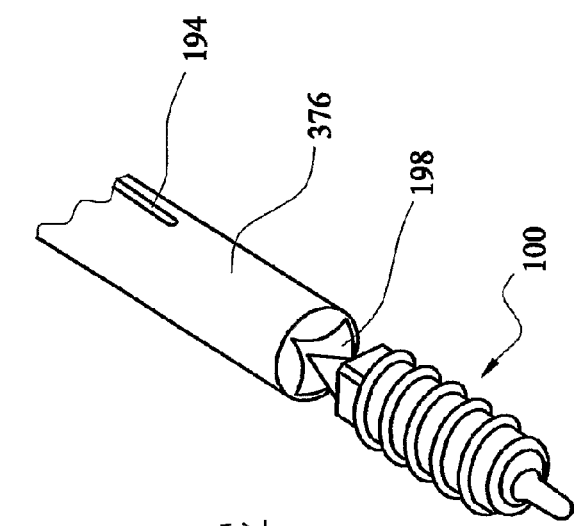

Either the insertion tool, or a drill bearing an adapter to provide the insertion tool, can be used. FIG. 14C shows the end 376 of the insertion tool or drill bearing an adapter. The free ends of suture 200 are passed through aperture 198 and out into channel 194 at step 346.

After the suture 200 has been engaged with the end of the insertion tool at step 346, then at step 348, the insertion tool assembly is pushed through the skin of the patient while applying tension to the free ends of the suture 200 so as to guide the instrument assembly toward the connector 114 on the proximal end of the implantable marker 100. At step 350, the distal end of the insertion tool is attached to the implantable marker and switch 362 can be operated so as to unscrew the implantable marker from the bone 372. The sutures 200 are kept under tension so as to keep the implantable marker connected to the distal end of the insertion tool. In an alternate embodiment, the implantable marker can be removed manually using a tool inserted through guide tube 164. At step 352, once the implantable marker has been unscrewed from the bone 372, the instrument assembly and implantable marker are withdrawn through the patient's skin 368.

The user can then determine whether there are any further implantable markers to be removed at step 354, and if so, the further implantable markers can be removed using the same method, as indicated by line 356. When it has been determined that all the implantable markers have been percutaneously removed, then at step 358, the method of removal 340 ends.

The implantable markers described above are trackable by the tracking system and therefore once they have been percutaneously implanted in the patient's bones, the position of the patient's bones can be tracked and displayed during a computer aided surgical procedure. It will be appreciated that no invasive surgical steps are required in order to implant the markers and therefore the implantable markers can be implanted before a surgical procedure and so can be carried out as a clinical, or out-patient procedure. For example, the implantable markers can be percutaneously implanted in the patient's bones several days or weeks before the surgical procedure.

Figure 15:
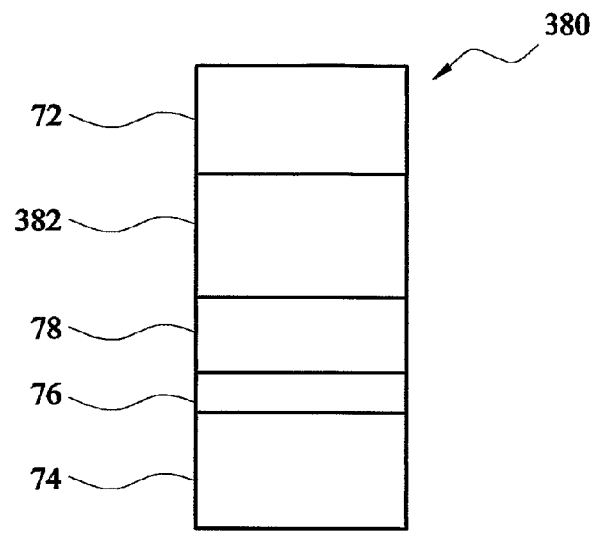
FIG. 15 shows a schematic representation of a marker part of an implantable marker according to an embodiment of the invention and including a sensor or transducer.

FIG. 15 shows a further embodiment of a marker part 380 of an implantable marker. Marker 380 is similar to marker 70 and includes sensor coils 72, circuitry 78, antenna 76 and RF power coils 74. However, marker 380 also includes a transducer 382 or other sensor for detecting a property in the region or area around where the marker has been implanted. Transducer or sensor 382 generates an electrical signal representative of the local property of the body and the signal is processed by circuitry 78 for transmission back to the tracking system using antenna 76. In other embodiments, the signal from the transducer can be transmitted back to the tracking system using a wire line system, e.g. a electrical conductor or optical conductor, such as a fibre optic cable.

Transducer or sensor 382 can be of many types, depending on the property to be measured. For example the body transducer 380 can be a pressure transducer which provide a measure of the local stress, a temperature sensor, which provides a measure of the local temperature, a biological activity sensor, which provides an indication of a biological activity (e.g. osteoblast activity) or a chemical sensor, which provides an indication of a local chemical property (e.g. pH). Other types of sensors for different kinds of properties can of course be used also.

Marker 382 may be wholly encapsulated by encapsulant material and/or a housing, or apertures may be provided in the encapsulant and/or housing in appropriate places to allow any sensor or detector parts of the transducer to have access to the local region of the body that it is intended to measure.

Figure 16:
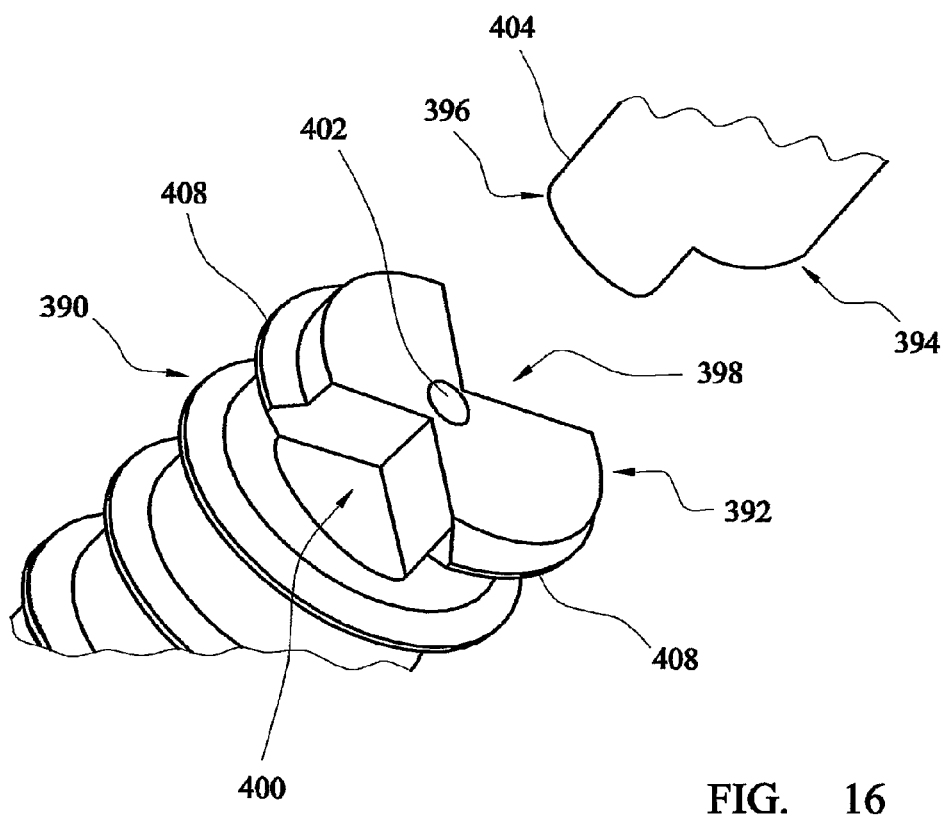
FIG. 16 shows a schematic representation of a distal end part of a further implantable marker illustrating a drive connector mechanism.

FIG. 16 shows a schematic representation of an end of a further implantable marker 390 in greater detail illustrating a further embodiment of a drive connector 392 by which an insertion tool 394 can releasably engage with the marker to apply torque to drive the marker into bone.

The interface between the distal end 396 of the insertion tool 394 and the implantable marker 390 is based on matching butterfly shaped formations in the mating ends of the insertion tool and implantable marker. The connector formation 392 of the marker includes first and second diametrically opposed, generally V shaped notches or recesses 398,400 in the end of the marker. Each recesses 398,400 has the general shape of a segment of a circle or of an annulus. Further, in this embodiment of the marker, a bore 402 runs at least partially along the longitudinal, central axis of the marker and can accept a suture secured therein and by which the marker can be extracted in a manner similar to that described above. The insertion tool includes first 404 and second prongs, or other extended elements, shaped to match and engage with the recesses 398, 400 so as to communicate drive from the insertion tool to the marker in use. The insertion tool also has a bore or channel extending along its longitudinal, central axis in which the suture attached to the marker can be received in use in a manner similar to that described above.

This drive interface has a number of advantageous properties. It allows the transmission of torque efficiently within a confined space. It allows the suture, or alternatively a wire for passing electrical signals, to be ideally centrally located. It allows the marker to be screwed flush into the bone and no 'head' protrudes from the bone surface once in place. It provides mechanical fixation over as much surface as possible. It provides for easy manufacture.

As the drive faces are radial to the screw, torque is transmitted in a tangential manner which is the most efficient. Also, forces are transmitted at the outer edge of the screw thread which also increases the efficiency of torque transmittal as the torque transmitted is the product of the force (F) and the radial distance (d) from the centre of rotation. From this, it also follows that, for a given torque, F is as low as possible, which is beneficial from the point of view of the strength of the drive connector and marker. Further, approximately half of the perimeter of the screw at the drive connector end maintains the thread form 408 thereby improving mechanical fixation in this area. Furthermore, bone ingrowth into the recesses 398, 400 is possible helping to prevent rotation thereby providing a locking action. Further again, the connector formation does not interfere with the central region of the end of the marker, allowing for the easy integration of the bore 402 for a suture, electrical wire, cannulation or other features.

Some curvature of the surfaces can be provided in order to accept tolerance variations. Sprung drive elements 404 on the insertion tool can be provided to help retain the marker on the drive instrument 394, in use, to allow for ease of operation, e.g. single handed use.

Figure 17A:
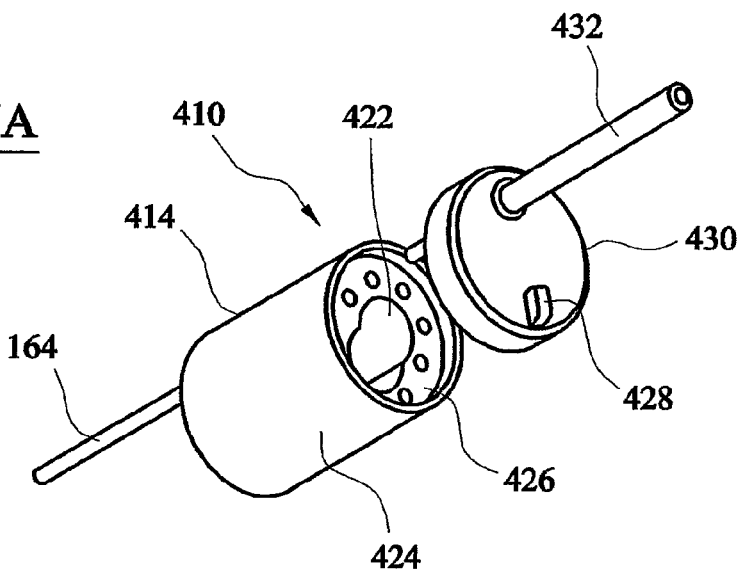
FIG. 17A shows a schematic exploded perspective view of a further embodiment of a guide instrument.
Figure 17B:
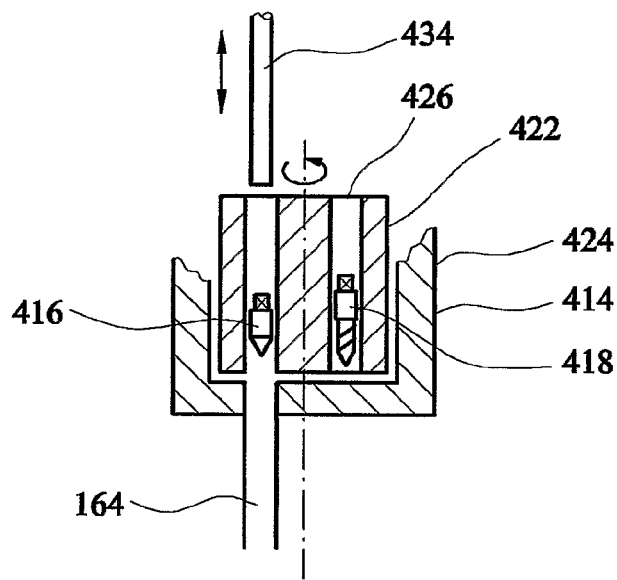
FIG. 17B shows a schematic cross sectional view through the magazine part of the guide instrument shown in FIG. 17A.
Figure 17C:
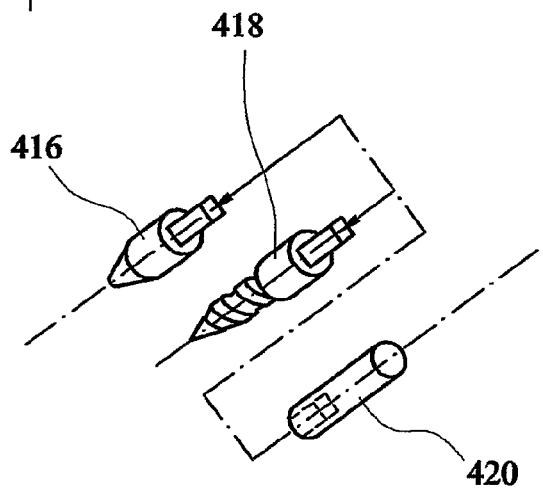
FIG. 17C shows a schematic illustration of a marker, a pre-drill and adapter parts useable with the guide instrument illustrated in FIGS. 17A and 17B.

FIG. 17A shows a further embodiment of a guide instrument 410. Guide instrument 410 is generally similar to guide instruments 160 and 300 except that its adapted to include a magazine 414 which can hold a plurality of implantable markers. FIG. 17B shows a schematic cross section through the magazine part 414 of the guide instrument 410. FIG. 17C shows a schematic illustration of a marker 416, a pre-drill 418 and adapter 420 parts useable with the guide instrument.

In the embodiment shown in FIGS. 17A and 17B, the magazine, or cartridge, part 414 of the guide instrument includes a drum 422, rotatably mounted in a generally circular housing 424. The drum 422 includes a plurality of bores, or channels, 426 therein and circumferentially disposed toward the edge of the drum 422. A lid, or closure, part 430 of the cartridge includes a button or switch 428 actuable by a user to cause a rotation mechanism (not shown) to operate so that the drum is rotated to place a next bore 426 in registration with the longitudinal axis of the guide tube 164 of the guide instrument. The lid 430 includes a tube 432 in registration with an aperture in the lid which is also in registration with the longitudinal axis of the guide tube 164. In use tube 432 can accept the distal end of the insertion instrument 434. The distal end of insertion instrument 434 includes a connector including an adapter 420 which can interface with a matching connector formation on the marker 416 and the drill bit 418.

Use of this embodiment of the guide instrument is similar to that described above. Initially, the insertion instrument 434 is engaged with the drill bit 418, which includes a trochanter tip, which protrudes from the distal end of the guide tube 164. The guide tube is pushed through the skin until it engages the patient's bone. A power unit attached to the insertion instrument is then operated to pre-drill a hole in the bone for receiving a marker. In other embodiments, a power unit can be provided as part of or internal to the guide instrument housing 424 which is operable to drive the insertion instrument. Once the hole has been drilled, the insertion instrument and drill bit are withdrawn and the drill bit 416 is retained in a one of the bores of the drum 422, as illustrated in FIG. 17B. The insertion instrument is removed from the bore, but not fully from the cartridge housing, so that actuation of button 428, causes the drum to rotate so that a marker 418, is presented. The insertion instrument is then introduced into the newly presented bore and engaged with the marker 416 which can then be driven into the pre-drilled hole.

In some embodiments, a single drill bit and multiple markers can be provided in the drum. In other embodiments, multiple drill bits and the same number of markers can be provided in the drum so that a new drill bit is used in the insertion of each marker. The drill bits and markers can be provided in alternating bores in the drum so that in use, either a drill bit or marker is automatically presented at the correct stage in the insertion sequence when the button 428 is actuated.

Hence, a plurality of implantable components can be pre-loaded, in a sterile condition, into the guide instrument and quickly inserted. The likelihood of contamination of, or damage to, the components is reduced as they components are positioned in the cartridge prior to use. The drill bit should not become contaminated as it is stored in the cartridge when not in use. Soft tissue irritation is kept to a minimum as the guide tube stays in place during drilling and implantation. Implantation of the marker can be carried out by a single person. The time required is also kept to a minimum and the marker can be implanted as an out patient procedure with only local anaesthetic. Further, the appearance of the procedure to the patient is less disturbing.

Figure 18:
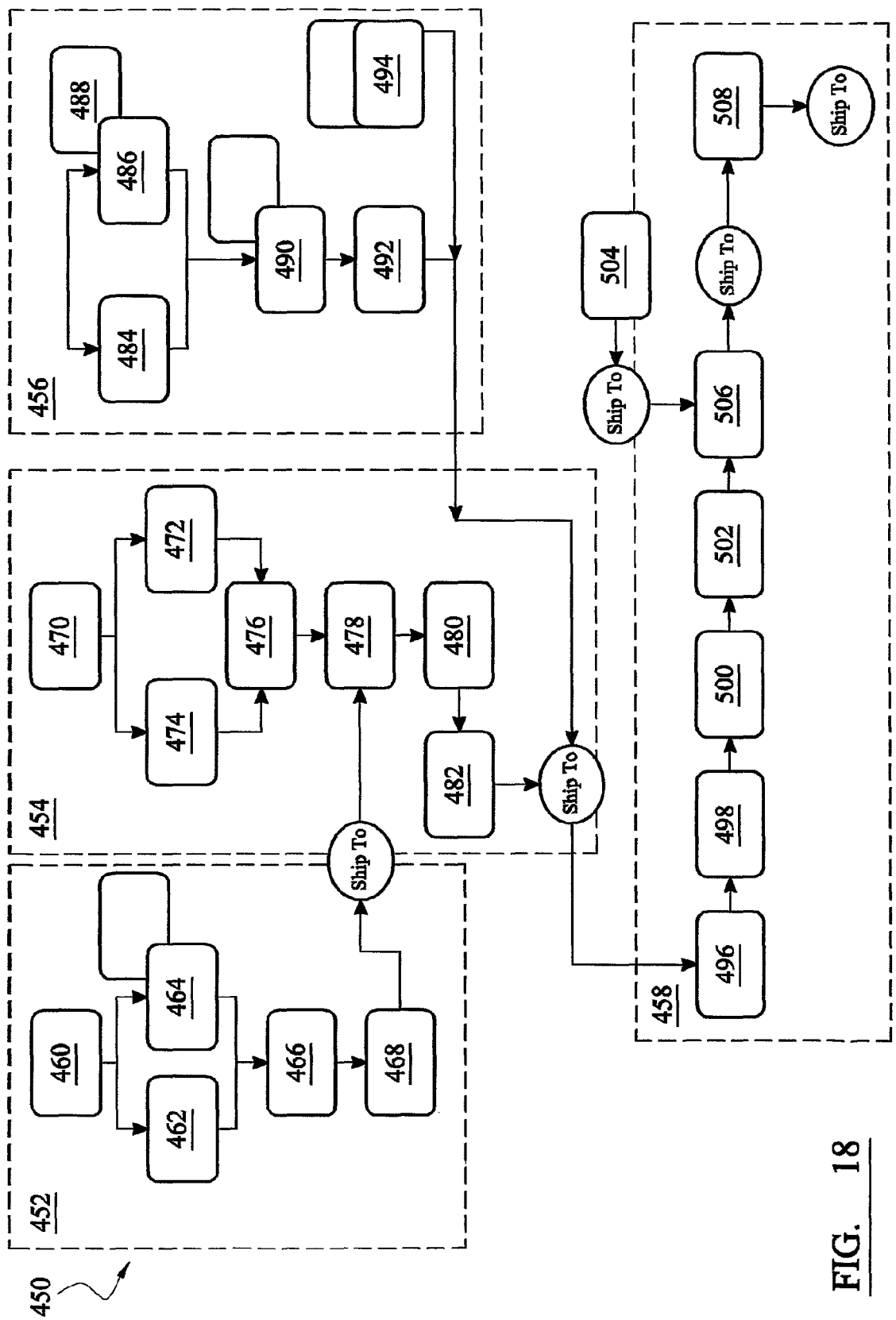
FIG. 18 shows a flow chart illustrating a method of manufacturing a marker according to the invention.

FIG. 18 shows a flow chart illustrating various steps in a method of manufacturing the marker as mentioned above in greater detail. The method includes four general areas of activity: coil manufacture 452; electronics manufacture 454; capsule or housing manufacture 456; and assembly 458 of the marker. As will be appreciated, some of the steps of the different activities can be carried out in parallel.

Coil manufacture 452 generally requires 460 ferrite cores, wire and the winding of the coils. Ferrite cores are supplied 462 and suitable wire is supplied 464 and at step 466 the sensor coils, RF power coils and any other coils required by the marker are assembled using a winding machine. Then at step 468, the coils are tested before being supplied to the electronics manufacturing process 454.

The electronics manufacturing process generally relates to manufacture of the microelectronic system of the marker 470. An application specific integrated circuit (ASIC) is supplied 472, as are the passive electronic components 474. A substrate for the printed circuit board (PCB) is also supplied 476 and at step 478, the coils, components and ASIC are mounted on and connected to the PCB. Then at step 480, the PCB assembly is folded and encapsulated in an epoxy. At step 482, the electronics are tested and the electronic assembly passed to a final assembly process 458.

The capsule or housing manufacturing process 456 includes the provision 484 of a titanium collar 102 and the provision 486 of a ceramic cup 106, or alternatively 488 a ceramic housing/capsule. Then at step 490, the titanium collar and ceramic cup or capsule are brazed together and at step the joint is leak tested. A titanium cap or nose part 104 is also provided at step 494 to complete the housing.

The electronics, and housing parts are then supplied to the assembly process 458 and at step 496 the electronics are located in the housing and at step 498 the titanium nose cap is laser welded to the housing to hermetically seal the housing. The at step 500, the assembled marker is leak tested using helium and if the leak testing is passed, then a final test of the electronics is carried out, the marker is calibrated and calibration data and marker ID data is written to and stored by the electronics at step 502. Calibration of the marker generally includes calibrating the sensor coils in a known magnetic field distribution so as to calibrate the position and orientation that the marker will report. If the marker is to be provided as part of a cartridge of multiple markers then a cartridge is supplied at step 504 and the marker is inserted into the cartridge together with any drill bits required. The assembled cartridge is then provided to a sterilisation facility at which the marker and cartridge are sterilised 508. The assembly can then be stored or supplied to a user.

As will be appreciated, the implantable marker, instruments and method of implantation allow a small marker to be accurately and reliably positioned in the bone of a patient so that the performance of that bone can be monitored using the tracking system. As the marker can be implanted through the skin, without requiring prior surgical intervention, the trauma involved with the implantation method of the present invention is minimised. Further, the marker is located more closely to, and intimately with, the bone whose position is to be tracked and therefore the accuracy of the positional data available from the marker is increased.

Once implanted, the implantable markers of the present invention can be left in the patient for many years, hence their position can be measured repeatedly over a significant time period to monitor the behaviour of a patient's bones, e.g. their limbs following joint surgery or orthopedic implants, such as knee, hip, shoulder, or spinal or other prosthetic implants.

Further, the implantable markers of the present invention can be implanted, effectively by injection, during an out patient procedure as a precursor to a subsequent scanning or surgical procedure. The implanted markers can then be detected by the scan and or during the surgical procedure and the position of the bones can be tracked and used during a computer aided or image guided surgical procedure.

It will be appreciated that a number of the features of the different embodiments of the marker described above can be altered and the different features described with respect to the different embodiments can be adapted and swapped between embodiments, and differently combined, such that the current invention should not be considered to be limited only to the specific embodiments described.

It will also be appreciated that, unless the context requires otherwise, a number of the steps of the method can be carried out substantially simultaneously, and they have been described as isolated steps in the preceding description merely so as to clarify the description of the method.

The invention claimed is:

1. A kit for percutaneously implanting an implantable marker in a bone, comprising:
   a guide instrument having a guide channel extending at least partially along a longitudinal axis thereof and for receiving an implantable marker therein, wherein the guide instrument includes a magazine for storing a plurality of implantable markers;
   an insertion tool receivable within the channel of the guide and translatable at least partially along the longitudinal axis, the insertion tool having a distal end for releasably engaging an implantable marker;
   an implantable marker receivable within the channel, the implantable marker comprising a housing defining a cavity and a marker detectable by a tracking system in the cavity, wherein the insertion tool is operable to drive the implantable marker into the bone, and the magazine includes a dispensing mechanism configured to automatically insert a further implantable marker into the guide channel after a current implantable marker has been implanted; and
   a drill receivable within the guide channel and translatable at least partially along the guide channel, the drill having a drill bit at a distal end for creating a hole in the bone.

2. The kit of clam 1, wherein the implantable marker has an outer surface, the outer surface providing a bone anchor configured to engage at least partially with surrounding bone when implanted in use to retain the implantable marker in the bone.

3. The kit claim 2, wherein the marker and cavity are configured such that at least a part of the marker is positioned within the bone in use.

4. The kit of claim 2, wherein the marker is hermetically sealed.

5. The kit of claim 2, wherein the bone anchor is in the form of a retaining formation.

6. The kit of claim 2, wherein the bone anchor is provided by a surface adapted to encourage bone on growth.

7. The kit of claim 2, wherein the marker is enclosed by the housing.

8. The kit of claim 2, wherein the marker is wirelessly detectable.

9. The kit of claim 8, wherein the marker is wirelessly detectable using electromagnetic radiation within the radio frequency portion of the electromagnetic spectrum.

10. The kit of claim 5, wherein the retaining formation includes at least a first barb.

11. The kit of claim 5, wherein the retaining formation includes a thread.

12. The kit of claim 2, wherein the housing has an insertion end which is tapered.

13. The kit of claim 12, wherein the insertion end is configured to be bone penetrating such that the implantable marker can be pushed into the bone when a force is applied to the implantable marker.

14. The kit of a claim 12, wherein the insertion end includes a self-taping screw thread.

15. The kit of claim 2, wherein the housing has a connector for releasably engaging with an insertion tool.

16. The kit of claim 14, wherein the connector is configured to prevent relative rotation between the implantable marker and an insertion tool, when connected to the insertion tool.

17. The kit of claim 11, wherein at least a first portion of the thread has a cross section shaped to enhance retention of the implantable marker in the bone.

18. The kit of claim 17, wherein at least a second portion of the thread has a cross section shaped to enhance cutting into the bone.

19. The kit of claim 17, wherein the first portion of the thread has a cross section in the shape of a rounded trapezium.

20. The kit of claim 1, wherein the insertion tool has an elongate body which includes a channel extending at least partially along the longitudinal axis of the elongate body for receiving a thread attached to the implantable marker.

21. The kit of claim 20, wherein the insertion tool has an aperture for receiving the thread therethrough.

22. The kit of claim 1, wherein the implantable marker has a distal end bearing a bone penetrating tip.

23. The kit of claim 1, wherein a distal end of the guide instrument has a bone engaging formation which includes a plurality of bone penetrating teeth and wherein at least a first and a second of the plurality of bone penetrating teeth face in opposite senses.

24. The kit of claim 1, wherein, when the kit is assembled into an assembly, the assembly includes a skin piercing tip extending from a distal end of the guide instrument, so that the assembly can puncture the skin of a subject.

25. The kit of claim 1, wherein the implantable marker has the skin piercing tip, such that when the kit is assembled into the assembly the implantable marker is located within the guide channel with the skin piercing tip extending from the distal end of the guide instrument.

26. The kit of claim 24, wherein the kit includes a drill locatable within the guide channel and having a drill bit, wherein the drill bit has the skin piercing tip, such that when the kit is assembled into the assembly the drill is located within the guide channel with the skin piercing tip extending from the distal end of the guide instrument.

27. A kit for percutaneously implanting an implantable marker in a bone, comprising:
  a guide instrument having a guide channel extending at least partially along a longitudinal axis thereof and for receiving an implantable marker therein;
  an insertion tool receivable within the channel of the guide and translatable at least partially along the longitudinal axis, the insertion tool having a distal end for releasably engaging an implantable marker;
  an implantable marker receivable within the channel, the implantable marker comprising a housing defining a cavity and a marker detectable by a tracking system in the cavity, wherein the insertion tool is operable to drive the implantable marker into the bone;
  a drill receivable within the guide channel and translatable at least partially along the guide channel, the drill having a drill bit at a distal end for creating a hole in the bone; and
  wherein the insertion tool includes the drill and wherein the distal end of the insertion tool is a separable part of the insertion tool into which at least the drill bit can be releasably fastened to provide the insertion tool.

28. A method for percutaneously implanting an implantable marker in a bone, wherein the marker is detectable by a tracking system, the method comprising:
  puncturing the skin with an instrument that includes a guide channel extending at least partially along a longitudinal axis of the instrument and positioning a distal end of the instrument adjacent the bone;
  drilling a hole in the bone by translating a drill at least partially along the guide channel of the instrument;
  driving the implantable marker into the hole in the bone from the instrument; and
  withdrawing the instrument while leaving the marker implanted within the bone.

29. The method of claim 28, wherein driving the implantable marker into the bone further comprises pushing the implantable marker into the bone.

30. The method of claim 28, wherein driving the implantable marker into the bone further comprises screwing the implantable marker into the bone.

31. The method of claim 28, wherein the implantable marker comprises:
  a housing having a body section, a distal end and a proximal end, wherein the body section is cylindrical and defines a cavity therein, the distal end is tapered, the proximal end has a connector for engaging an insertion tool, and wherein the housing has an outer surface bearing a screw thread; and
  a marker enclosed within the cavity, the marker being hermetically sealed and wirelessly detectable by a tracking system using electromagnetic radiation within the radio frequency part of the electromagnetic spectrum, and wherein the implantable marker is retained in the bone in use by the interaction of the screw thread and surrounding bone and wherein the marker and cavity are configured such that the marker is located within the surrounding bone when the implantable marker is implanted in the bone in use.

32. The method of claim 28, wherein the implantable marker further comprises a transducer or sensor for detecting a property in the region around the marker.

33. The method of claim 32, wherein the sensor or transducer is sensitive to a property selected from the group consisting of pressure, temperature, biological activity, and chemical.

34. A kit for percutaneously implanting an implantable marker in a bone, comprising:
  a guide instrument having a guide channel extending at least partially along a longitudinal axis thereof and for receiving an implantable marker therein, wherein the guide instrument includes a magazine for storing a plurality of implantable markers and wherein a distal end of the guide instrument has a bone engaging formation which includes a plurality of bone penetrating teeth and wherein at least a first and a second of the plurality of bone penetrating teeth face in opposite senses;
  an insertion tool receivable within the channel of the guide and translatable at least partially along the longitudinal axis, the insertion tool having a distal end for releasably engaging an implantable marker; and
  an implantable marker receivable within the channel, the implantable marker comprising a housing defining a cavity and a marker detectable by a tracking system in the cavity, wherein the insertion tool is operable to drive the implantable marker into the bone, and the magazine includes a dispensing mechanism configured to automatically insert a further implantable marker into the guide channel after a current implantable marker has been implanted.

35. A kit for percutaneously implanting an implantable marker in a bone, comprising:
  a guide instrument having a guide channel extending at least partially along a longitudinal axis thereof and for receiving an implantable marker therein, wherein the guide instrument includes a magazine for storing a plurality of implantable markers;
  an insertion tool receivable within the channel of the guide and translatable at least partially along the longitudinal axis, the insertion tool having a distal end for releasably engaging an implantable marker;

an implantable marker receivable within the channel, the implantable marker comprising a housing defining a cavity and a marker detectable by a tracking system in the cavity, wherein the insertion tool is operable to drive the implantable marker into the bone, and the magazine includes a dispensing mechanism configured to automatically insert a further implantable marker into the guide channel after a current implantable marker has been implanted; and a drill locatable within the guide channel, the drill having a drill bit having a skin piercing tip, and wherein, when the kit is assembled into an assembly, the drill is located within the guide channel and the drill tip extends from a distal end of the guide instrument so that the assembly can puncture the skin of a subject.

* * * * *